(12) United States Patent
Garland et al.

(10) Patent No.: US 8,853,227 B2
(45) Date of Patent: Oct. 7, 2014

(54) METHOTREXATE ADJUVANTS TO REDUCE TOXICITY AND METHODS FOR USING THE SAME

(75) Inventors: William A. Garland, San Clemente, CA (US); Brian D. Frenzel, Los Altos, CA (US); Travis Karg, Laguna Niguel, CA (US)

(73) Assignee: Tosk, Incorporated, Santa Cruz, CA (US)

(*) Notice: Subject to any disclaimer, the term of this patent is extended or adjusted under 35 U.S.C. 154(b) by 135 days.

(21) Appl. No.: 13/164,686

(22) Filed: Jun. 20, 2011

(65) Prior Publication Data
US 2011/0319419 A1 Dec. 29, 2011

Related U.S. Application Data

(63) Continuation of application No. 12/396,388, filed on Mar. 2, 2009, now Pat. No. 7,998,967.

(60) Provisional application No. 61/033,333, filed on Mar. 3, 2008.

(51) Int. Cl.
*A61K 31/519* (2006.01)
*A61K 45/06* (2006.01)
*A61K 31/7068* (2006.01)

(52) U.S. Cl.
CPC .............. *A61K 31/519* (2013.01); *A61K 45/06* (2013.01); *A61K 31/7068* (2013.01)
USPC ...................................................... 514/267

(58) Field of Classification Search
None
See application file for complete search history.

(56) References Cited

U.S. PATENT DOCUMENTS

| | | | |
|---|---|---|---|
| 5,296,216 A | 3/1994 | Turner | |
| 5,736,531 A | 4/1998 | von Borstel et al. | |
| 5,968,914 A * | 10/1999 | von Borstel et al. | 514/50 |
| 6,066,668 A | 5/2000 | Hausheer et al. | |
| 6,344,447 B2 | 2/2002 | von Borstel et al. | |
| 6,992,072 B2 | 1/2006 | Walker | |
| 7,166,581 B1 | 1/2007 | von Borstel et al. | |
| 7,709,459 B2 | 5/2010 | von Borstel et al. | |
| 7,998,967 B2 * | 8/2011 | Garland et al. | 514/267 |

FOREIGN PATENT DOCUMENTS

| | | |
|---|---|---|
| JP | H06508846 A | 10/1994 |
| JP | H10511689 A | 11/1998 |
| WO | 9426761 | 11/1994 |
| WO | 03099297 | 12/2003 |

OTHER PUBLICATIONS

Verses, et al., Inhibition of uridine phosphorylase by pyrimidne nucleoside analogs and consideration of substrate binding to the enzyme based on solution conformation as seen by NMR spectroscopy, 1988, Eur. J. Biochem., 178, pp. 173-181.*
Martin et al., Use of oral uridine as a substitut for parenteral uridine rescue of 5-fluorouracil therapy, with and without the uridine phosphorylase inhibitor 5-benzylacyclouridine, 1989, Caner Chemother. Pharmacol., 24, pp. 9-14.*
Ashour et al., "5-(m-Benzyloxynezyl) barbituric Acid Acyclonucleoside, a Uridine Phosphorylase Inhibitor, and 2', 3', 5'-Tri-O-Acetyluridine, a Prodrug of Uridine, as Modulators of Plasma Uridine Concentration"; Biochemical Pharmacology; vol. 51, pp. 1601-1611 (1996).
Ashour et al., "Effect of 5-(phenylselenenyl) acyclouridine, an inhibitor of uridine phosphorylase, on plasma concentration of uridine released from 2', 3', 4'—tri-O-acetyluridine, a prodrug of uridine: releavance to uridine rescue in chemotherapy"; Cancer Chemo. Pharmacol. (2000): 46:235-240.
Ashour et al., "Modulation of 5-Fluorouracil Host Toxicity by 5-(Benzyloxynezyl) barbituric Acid Acyclonucleoside, a Uridine Phosphorylase Inhibitor, and 2', 3', 5'—Tri-O-Acetyluridine, a Prodrug of Uridine"; Biochemical Pharmacol. vol. 60, pp. 427-431 (2000).
Brunetti et al., "5-Fluorouracil Enhances Azidothymidine Cytotoxicity: In Vitro, In Vivo, and Biochemical Studies"; Cancer Research 50: 4026-4031 (1990).
Christensen et al., "Effect of Hydration and Methotrexate Plasma Concentrations in Children With Acute Lymphocytic Leukemia"; J. Clin Oncology 6:797-801 (1988).
Darnowski et al., "Fluorouracil plus azidothynidine cytotoxicity in vitro: Relationship to cellular thymidine kinase activity"; Proc. of American Assoc. for Cancer Research; vol. 31: 398 (1990).
Darnowski et al., "Resistance to Azido-Thymidine Cytotoxicity in the Human Colon Tumor Cell Line HCT15 is Associated with Enhanced Removal of AZT from Cellular DNA"; Proc. of American Assoc. for Cancer Research; vol. 32: 358 (1991).
Drabikowska et al., "Inhibitor Properties of Some 5-Substituted Uracil Acyclonucleosides, and 2,2'-Anhydrouridines Versus Uridine Phosphorylase From *E. coli* and Mammalian Sources"; Biochemical Pharmacology, vol. 36, No. 23: 4125-4128 (1987).
Howell et al., "Thymidine Rescue of High-Dose Methotrexate in Humans"; Cancer Research 38: 325-330 (1978).
Howell et al., "Cytokinetic Comparison of Thymidine and Leucovorin Rescue of Marrow in Humans after Exposure to High-Dose Methotrexate"; Cancer Research 39: 1315-1320 (1979).
Iigo et al., "Differential Effects of 2,2'-Anhydro-5-Ethyluridine, A Uridine Phosphorylase Inhibitor, On the Antitumor Activity of 5-Fluorouridine and 5-Fluoro-2'-Deoxyuridine"; Biochemical Pharmacol. vol. 39, No. 7: 1247-1253 (1990).
Martin et al., "High-Dose 5-Fluorouracil with Delayed Uridine 'Rescue' in Mice"; Cancer Research 42: 3964-3970 (1982).

(Continued)

*Primary Examiner* — Jason Sims
*Assistant Examiner* — Tori M Strong
(74) *Attorney, Agent, or Firm* — Bret E. Field; Bozicevic, Field & Francis LLP

(57) ABSTRACT

Methods are provided for using methotrexate (MTX) active agents in which reduced host toxicity is observed. Aspects of the methods include administering to a subject an effective amount of an MTX active agent in conjunction with a MTX toxicity-reducing adjuvant, such as a 2,2'-anhydropyrimidine, a derivative thereof or a uridine phosphorylase inhibitor. Also provided are compositions and kits that find use in practicing embodiments of the invention. The methods and compositions find use in a variety of applications, including the treatment of a variety of different disease conditions.

17 Claims, 7 Drawing Sheets

(56) References Cited

OTHER PUBLICATIONS

Martin et al., "Use of oral uridine as a substitute for parenteral uridine rescue of 5-fluorouracil therapy, with and without the uridine phosphorylase inhibitor 5-benzylacyclouridine"; Cancer Cemotherapy Pharmacol. 24: 9-14 (1989).

Newman et al., "Increased Sensitivity to Azidothymidine in a Subline of CCRF-CEM Human Leukemia Cells Resistant to Methotrexate"; Proceedings of the American Assoc. for Cancer Research vol. 32: 413 (1991).

Pizzorno et al., "Phase I Clinical and Pharmacological Studies of Benzylacyclouridine, a Uridine Phosphorylase Inhibitor"; Clinical Cancer Research vol. 4: 1165-1175 (1998).

Scanlon et al., "Overexpression of DNA Replication and Repair Enzymes in Cisplatin-Resistant Human Colon Carcinoma HCT8 Cells and Circumvention by Azidothymidine"; Cancer Communications vol. 1, No. 4: 269-275 (1989).

Semon et al., "Potentiation of the Antitumor Activity of Methotrexate by Concurrent Infusion of Thymidine"; Cancer Research 38: 2905-2911 (1978).

Sterba et al., "High-dose methotrexate and/or leucovorin rescue for the treatment of children with lymphoblastic malignancies: do we really know why, when and how?"; Neoplasma 52: 6 (2005) 456-463.

Tattersall et al., "The reversal of methotrexate toxicity by thymidine with maintenance of antitumour effects"; Nature 17:253 (5488): 198 (1975).

Tosi et al., "Azidothymidine-induced Cytotoxicity and Incorporation into DNA in the Human Colon Tumor Cell Line HCT-8 is Enhanced by Methotrexate in Vitro and in Vivo"; Cancer Research 52; 4069-4073 (1992).

Veres et al., "Inhibition of uridine phosphorylase by pyrimidine nucleoside analogs and consideration of substrate binding to the enzyme based on solution conformation as seen by NMR spectroscopy"; Eur. J. Biochem. 178: 173-181 (1988).

Weber et al., "Azidothymidine Inhibition of Thymidine Kinase and Synergistic Cytotoxicity with MethoTrexate and 5-Fluorouracil in Rat Hepatoma and Human Colon Cancer Cells"; Cancer Communications vol. 2: 129-133 (1990).

Weber et al., "AZT: A Biochemical Response Modifier of Methotrexate and 5-Fluorouracil Cytotoxicity in Human Ovarian and Pancreatic Carcinoma Cells"; Cancer Communications vol. 3, No. 4: 127-132 (1991).

Weber et al., "Regulation of De Novo and Salvage Pathways in Chemotherapy"; Adv. Enzyme Regul. 31: 45-67 (1991).

Stella. Prodrugs as therapeutics. Expert Opinion on Therapeutic Patents, 2004, vol. 14, No. 3, pp. 277-280.

Wolff. Burger's Medicinal Chemistry and Drug Discovery, 1994, 5th edition, vol. 1, pp. 975-977.

Testa. Prodrug research: futile or fertile? Biochemical Pharmacology, 2004, vol. 68, pp. 2097-2106.

Ettmayer, et al. Lessons learned from marketed and investigational prodrugs. Medicinal Chemistry, 2004, vol. 47, No. 10, pp. 2394-2404.

Morissette, et al. High-throughput crystallization: polymorphs, salts, co-crystals and solvates of pharmaceutical solids. Adv Drug Deliv Rev. Feb. 23, 2004;56(3):275-300.

Vippagunta, et al. Crystalline solids. Adv Drug Deliv Rev. May 16, 2001;48(1):3-26.

Mazokopakis et al., "Wild chamomile (*Matricaria recutita* L) mouthwashes in methotrexate- induced oral mucositis" Phytomedicine, Gustav Fischer Verlag, Stuttgart, DE vol. 12, No. 1-2 (2005) pp. 25-27.

Veres et al., "5-Substituted-2,2'-anhydrouridines, potent inhibitors of uridine phosphorylase" Biochemical Pharmacology, Pergamon, Oxford GB, vol. 34, No. 10 (1985) pp. 1737-1740.

\* cited by examiner

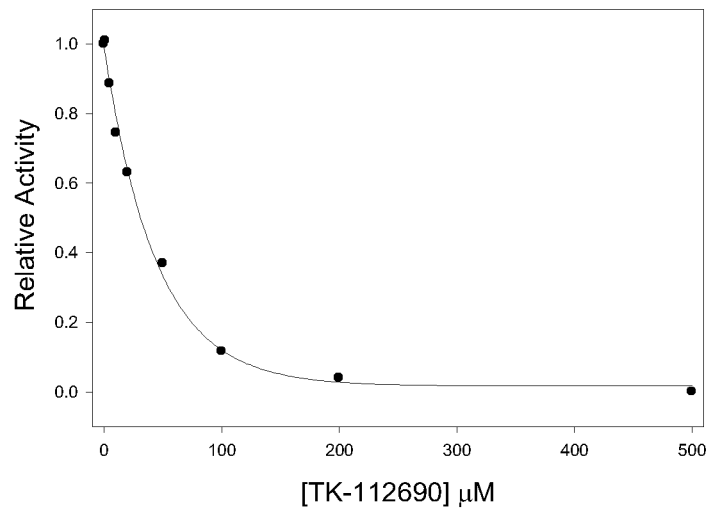
FIGURE 10
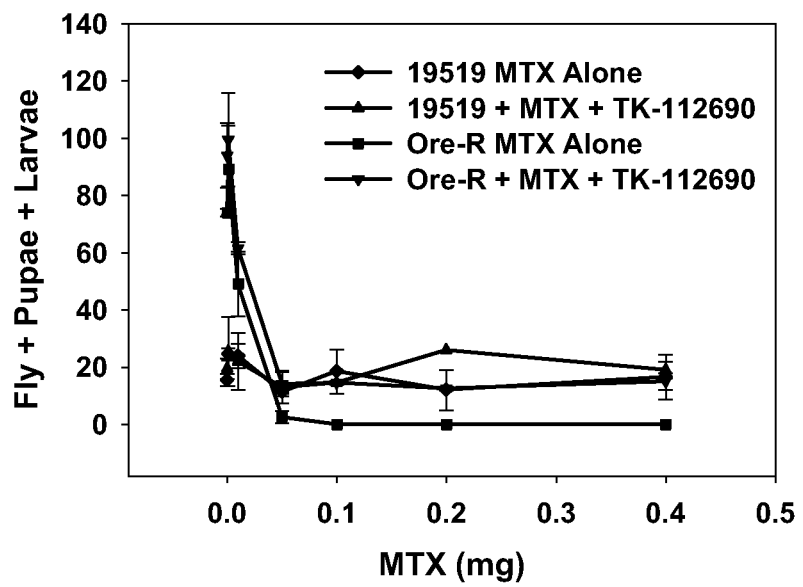

120 mg/kg TK-112690 ip to CD-1 mice
Top Line = Plasma TK-112690 (μg/ml); Bottom Line = Plasma Uridine (μg/ml)

METHOTREXATE ADJUVANTS TO REDUCE TOXICITY AND METHODS FOR USING THE SAME

CROSS-REFERENCE TO RELATED APPLICATIONS

Pursuant to 35 U.S.C. §119 (e), this application claims priority to the filing date of U.S. Provisional Patent Application Ser. No. 61/033,333 filed Mar. 3, 2008; the disclosure of which application is herein incorporated by reference.

INTRODUCTION

The presence of tetrahydrofolates (THFs) in cells provides important life-sustaining processes, such as the biosynthesis, replication and repair of DNA and RNA. THFs perform this function by providing substrates required to complete the biochemical reactions facilitating these processes. THFs are biosynthesized intracellularly through reduction of folic acid by the enzyme dihydrofolate reductase (DHFR) or other dihydrofolate intermediates. The pteridine compound, methotrexate (MTX; N-[4-[[(2,4-diamino-6-pteridinyl)methyl] methylamino]benzoyl]-L-glutamic acid), is structurally similar to folic acid (see structures for Folic acid and MTX below).

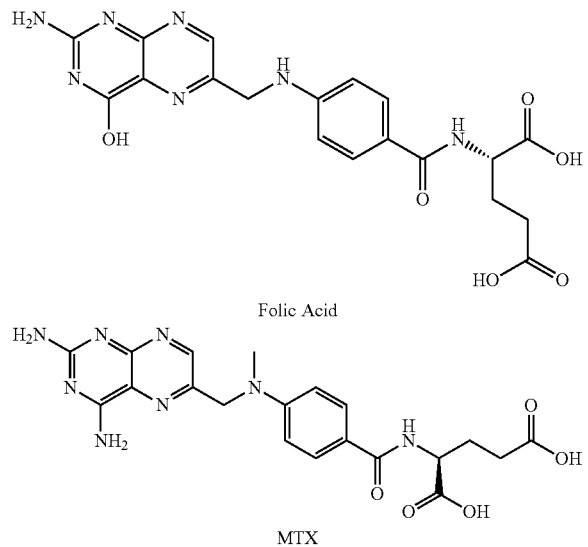

As a result, MTX can bind to active sites on DHFR and block, by competitive inhibition, the formation of THFs needed for the de novo synthesis of the nucleoside thymidine, required for DNA synthesis. Also, folate is needed for purine base synthesis, so all purine synthesis will be inhibited. Methotrexate, therefore, inhibits the synthesis of DNA, RNA, thymidylates, and proteins and the ability of MTX to inhibit nucleic acid synthesis has been exploited for over 50 years in the treatment of aberrant cell growth ((Jolivet et al., N Engl J Med; 309:1094-1104 (1983); Gangjee, Anti-Cancer Agents in Medicinal Chemistry; 7: 524-542 (2007); Assaraf, Metastasis Review; 26: 153-181 (2007); Huennekens; Advanced Enzyme Regulation; 34: 397-419 (1994); Walling, Investigational New Drugs; 24: 37-77 (2006); Gangjee, Jain, Hiteshkumar, Current Medicinal Chemistry; 4: 405-410 (2004)). In particular, malignant cells typically have a greater need for THFs than normal cells because they proliferate more rapidly and are therefore more sensitive to the effect of MTX. In many cases, MTX can be used to selectively impair cancerous cell growth without damaging normal cell growth. As a result of its effectiveness against rapidly proliferating cells, MTX is one of the most widely used anticancer agents indicated for the treatment of both solid and hematological cancers. For example, MTX is employed alone or with other treatment modalities in the treatment of neoplastic diseases such as gestational choriocarcinoma, chorioadenoma destruens, hydatidiform mole, leukemias (for example, acute lymphocytic leukemia), breast carcinoma, epidermoid cancers of the head and neck, advanced mycosis fungoides (cutaneous T-cell lymphoma), lung carcinoma, non-Hodgkins lymphomas and trophoblastic neoplasms such as choriocarcinoma, chorioadenoma destruens, hydatidiform mole (Physicians Desk Reference, 60th ed., Thomson Healthcare, Stamford, Conn. (2006); Goodman & Gilman's The Pharmacological Basis of Therapeutics, $11^{th}$ ed., McGraw-Hill Columbus, Ohio (2005); The Merck Manual of Diagnosis and Therapy 18th ed., John Wiley, Hoboken, N.J., (2006)).

Moreover, MTX is an effective immunosuppressive agent which can be used for the prevention of the graft-versus-host disease resulting from tissue transplants, as well as for the treatment of inflammatory diseases such as psoriasis, psoriatic arthritis, rheumatoid arthritis and Crohn's disease (Kokuryo). MTX is frequently used for the treatment of severe and disabling cases of psoriasis and rheumatoid arthritis (Warren et al., Br. J. Dermatology, 153(5), 869-873 (2005); Cronstein, Pharmacol. Rev., 57(2), 163-172 (2005)).

The numerous patents that have been issued disclosing MTX and MTX analogs, methods of synthesizing MTX or analogs thereof, and uses for MTX attest to the significance of MTX in treatment of aberrant cell growth. For example, U.S. Pat. No. 2,512,572 covers the active agent MTX, and U.S. Pat. Nos. 3,892,801, 3,989,703, 4,057,548, 4,067,867, 4,079, 056, 4,080,325, 4,136,101, 4,224,446, 4,306,064, 4,374,987, 4,421,913, and 4,767,859 claim methods for preparing MTX or potential intermediates in the synthesis of MTX. Other patents disclose labeled analogs of MTX, such as U.S. Pat. Nos. 3,981,983, 4,043,759, 4,093,607, 4,279,992, 4,376,767, 4,401,592, 4,489,065, 4,622,218, 4,625,014, 4,638,045, 4,671,958, 4,699,784, 4,785,080, 4,816,395, 4,886,780, 4,918,165, 4,925,662, 4,939,240, 4,983,586, 4,997,913, 5,024,998, 5,028,697, 5,030,719, 5,057,313, 5,059,413, 5,082,928, 5,106,950, and 5,108,987, wherein MTX is bound to a radionucleotide or fluorescent label, amino acid, polypeptide, transferrin or ceruloplasmin, chondroitin or chondroitin sulfate, antibody, or binding partner for a specific cell-surface receptor of target cells for use in assays of MTX, in timed-release of MTX, as toxins selective for cancer cells, or to facilitate transport of MTX across membranes or in vivo barriers.

Of the numerous patents issued disclosing methods of using MTX, a variety of patents such as U.S. Pat. Nos. 4,106, 488, 4,558,690, and 4,662,359 disclose methods of using MTX to treat cancer.

Unfortunately, given the effectiveness and broad applications of MTX therapy, treatment with this agent involves serious side-effects with significant risk to the patient. Since MTX interferes with cell replication and division, actively proliferating, non-malignant tissues such as intestinal mucosa and bone marrow are sensitive to MTX and may demonstrate impaired growth due to MTX treatment. MTX and a metabolite of methotrexate, 7-OH-MTX, are also associated with renal and hepatic toxicity when applied in the "high dose regimen" that is typically required for maximum efficiency (Barak et al., J. American Coll. Nutr., 3, 93-96 (1984); Yazici et al., J. Rheumatol. 29(8), 1586-1589 (2002)).

Damage to the gastrointestinal mucosa is the most debilitating of the side-effects of MTX. Known as mucositis, this complication may occur in the oral cavity or any other part of the alimentary canal ((Sonis et al., Cancer, 100:1995-2025 (2004)). A type of mucositis that is particularly troublesome for patients is stomatitis, ulceration of the mucosa in the mouth, a condition making eating and swallowing painful and difficult.

Mucositis decreases the quality of life of cancer patients receiving chemotherapy while increasing their risk of hospitalization (Naidu et al. Neoplasia, 6:423-31 (2004)). It can also result in serious bacterial infection (Pico et al., Oncologist 3: 446-451 (1998), and McGuire, Support Care Cancer, 11: 435-41 (2003)), often leading to the need to use a feeding tube (Treister and Sonis, Curr Opin Otolaryngol Head Neck Surg.; 15:123-9 (2007)). These complications frequently lead to reduced doses, or complete cessation, of the chemotherapy thereby reducing the efficacy of the chemotherapy (Sonis et al., Cancer. 100:1995-2025 (2004)). Increased need for medical care due to mucositis also results in added costs (Scully, Sonis, Diz, Oral Dis.; 12: 229-41 (2006)). There is no effective prophylaxis or treatment for mucositis (Sonis et al., Rev Cancer. 4: 277-284 (2004). Therefore, an adjuvant that ameliorates chemotherapy-induced mucositis could improve patients' quality of life and prognosis while reducing the financial burden of cancer therapy.

SUMMARY

Methods of using adjuvants to reduce the toxicity of methotrexate (MTX) in a host are provided. In the subject methods, an effective amount of an MTX active agent is administered to a host in conjunction with the administration of an MTX toxicity-reducing adjuvant of the present invention, where the MTX active agent and MTX toxicity reducing adjuvant may be administered sequentially, starting with either the MTX agent or the toxicity-reducing adjuvant, simultaneously, or a combination thereof. In certain embodiments, the MTX toxicity-reducing adjuvant is a 2,2'-anhydropyrimidine, a derivative thereof or a uridine phosphorylase (UPase) inhibitor. Also provided are compositions for use in practicing the subject methods, e.g., MTX pharmaceutical compositions having reduced toxicity and kits that include the same. The subject methods and compositions find use in a variety of different applications, including the treatment of a variety of different disease conditions. An exemplary application illustrating a significant advantage of the methods and compositions of the invention is the reduction of MTX-induced mucositis.

BRIEF DESCRIPTION OF THE FIGURES

In FIG. 7, the top chart provides the $IC_{50}$ curve for AS283 human lymphoma cells treated for 72 hours with either MTX or MTX+TK-112690 at a concentration of 100 and 10 µM (Top Chart) or while the bottom chart provides the $IC_{50}$ curve for MTX and MTX+TK-112690 1.0 µM.

Figure 1:
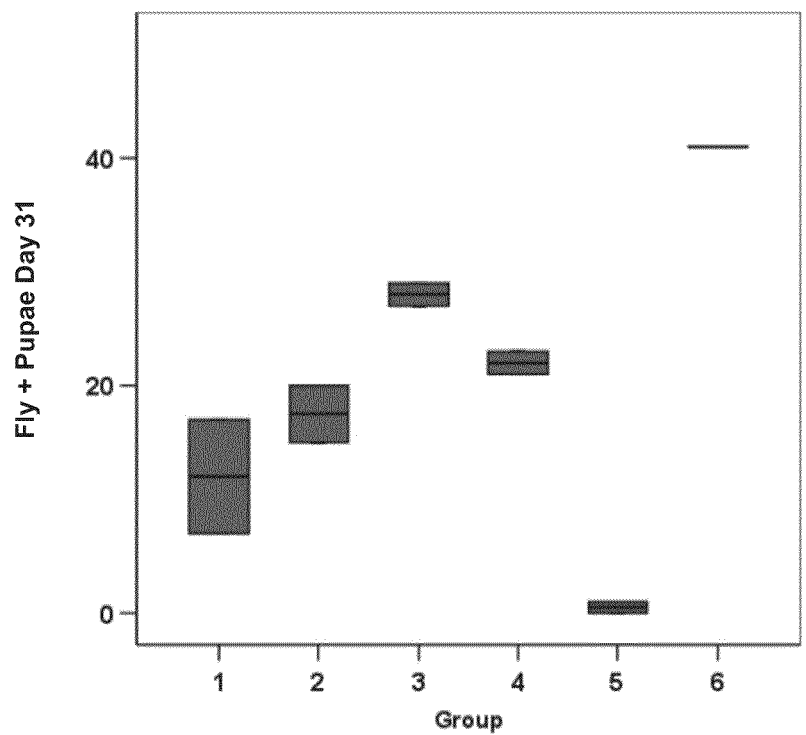
FIG. 1 depicts a set of results demonstrating the ability of TK-112690, a 2,2'-anhydropyrimidine MTX toxicity-reducing adjuvant according to an embodiment of the invention, to reduce MTX toxicity in flies (viability). In this study, *Drosophila melanogaster* eggs (50 eggs per vial) were treated with either 0.005 mg TK-112690+0.4 mg MTX (Group 1), 0.01 mg TK-112690+0.4 mg MTX (Group 2), 0.04 mg TK-112690+0.4 mg MTX (Group 3), 0.1 mg TK-112690+0.4 mg MTX (Group 4), 0.4 mg MTX alone (Group 5) or saline blank (Group 6). Two vials of eggs for each dose group were evaluated for viability (viable flies plus pupae).

TK-112690 was administered by ip injection [twice every 2 days for 5 injections with six hour interval (q6h×2, q2d×5)] at a dosage of 30 mg/kg/injection. MTX was administered by ip injection q2d×5 at a dosage of 5.0 mg/kg/injection three hours after the TK-112690 injection. The control group was treated with both vehicles, which were administered on the corresponding compound schedules.

The subcutaneous (sc) tumors were measured and the animals were weighed thrice weekly starting the day of the first treatment. The study was terminated twenty one days after tumor implantation. Tumors in the vehicle-treated control group grew to the evaluation point in all ten mice. The median tumor reached 4,387 mg in 21 days. The MTX treatment delayed the growth of AS283 lymphoma xenografts with a median tumor weight value 2.8% of the control on day 21 and a median tumor weight value of 24.7% (40.0 mg) smaller than the median tumor weight value at the start of treatment (162 mg). Administration of TK-112690 combined with MTX delayed the growth with a median tumor weight value 3.5% of the control on day 21 and a median tumor weight value 5.6% (9.0 mg) smaller than the median tumor weight value at the start of treatment (162 mg). There was no statistical difference between the MTX (Group 2) and MTX+TK-112690 (Group 3) tumor volumes (p=1.0) but both groups were statistically highly different (p<0.01) than the tumor volumes for the saline treated animals (Group1). Both groups receiving MTX were statistically identical using Bonferroni one-way ANOVA. Boxplots show the group median (black line), inter-quartile range (box) and outliers.

Figure 9:
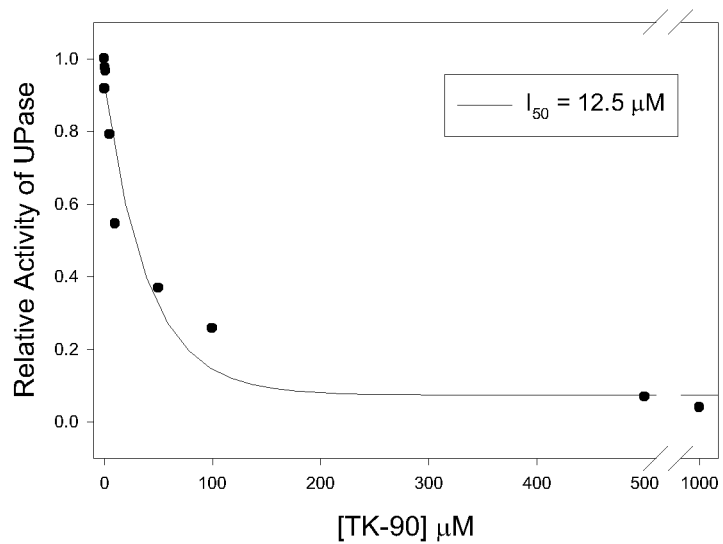

FIG. 9 depicts a set of data demonstrating that TK-112690, a 2,2'-anhydropyrimidine MTX toxicity-reducing adjuvant according to an embodiment of the invention inhibits both murine and human uridine phosphorylase (UPase). A range of TK-112690 doses were studied for the their ability to prevent metabolic breakdown of uridine through the in vitro inhibition of mouse and human small intestinal UPase enzyme. UPase activity was determined by HPLC analysis using UV detection of uracil concentration (UPase catabolizes uridine into uracil and ribose-1-phosphate). The UPase enzyme material was prepared from homogenized mouse and human being small intestinal tissue. TK-112690 was dissolved in water (50 mg/ml) and analyzed for UPase inhibition in aqueous solution containing 5 mM uridine, 0.01 M Tris, 0.01 M phosphate, 1 mM EDTA, and 1 mM DTT. Reactions were performed at 37° C. at pH of 7.3.

TK-11260 inhibition of mouse and human UPase was determined from measurements of uracil determined in homogenates by reverse phase HPLC using UV detection. The results demonstrate that TK-112690 inhibits mouse small intestinal UPase enzyme, with a $IC_{50}$ value of 12.5 µM. TK-112690 inhibits human small intestinal UPase enzyme, with a an $IC_{50}$ value of 20.0 µM.

FIG. 10 depicts a set of data further demonstrating that TK-112690, a 2,2'-anhydropyrimidine MTX toxicity-reducing adjuvant according to an embodiment of the invention, is a uridine phosphorylase (UPase) inhibitor. Embryos of UPase knockout (19519) *Drosophila melanogaster* were orally exposed to a dose range of MTX doses in food admix. Embryos of Wild-type (Oregon-R) were orally exposed to the same dose range of MTX in presence and absence of 0.04 mg TK-112690. Scoring was based on life or death 15 days after initiation of MTX exposure. UPase knockout *D. melanogaster* (19519) was seen to be resistant to lethal effects of a dose-range (0.001, 0.01, 0.05, 0.1, 0.2, 0.4 mg) of orally administered MTX. Wild-type *D. melanogaster* are sensitive to lethal effects of 0.1 mg MTX. Wild-type *D. melanogaster* are resistant to lethal effects of a dose-range (0.001, 0.01, 0.05, 0.1, 0.2, 0.4 mg) of orally administered MTX in the presence of 0.04 mg TK-112690.

As seen in FIG. 10, Methotrexate doses 0.1 mg are lethal to wild-type flies 15 days after the initiation of MTX exposure. Inhibition of UPase activity by the addition of 0.04 mg TK-112690 provides protection of lethality from doses as high as 0.4 mg of methotrexate. UPase mutant flies administered a dose range of methotrexate exhibit similar protection from methotrexate lethality as seen in wild-type flies administered methotrexate combined with TK-112690. Furthermore, the addition of TK-112690 into UPase mutant flies treated with a dose range of methotrexate does not provide added protection from methotrexate toxicities.

Figure 11:
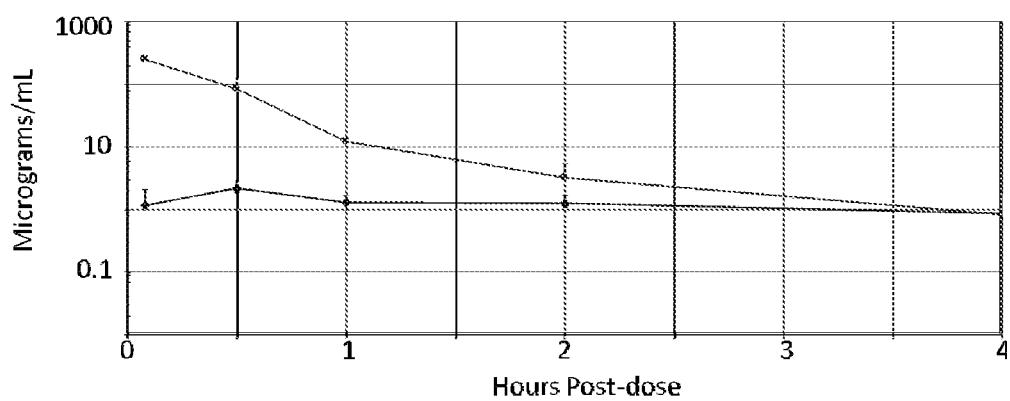

FIG. 11 depicts a set of data demonstrating that TK-112690, a 2,2'-anhydropyrimidine MTX toxicity-reducing adjuvant according to an embodiment of the invention, increased concentrations of uridine when administered to mice. In this study, CD-1 female mice were injected ip with 120 mg/kg TK-112690 and plasma from the animals analyzed by HPLC using UV detection for TK-112690 and uridine. Concentrations of uridine and TK-112690 in plasma samples collected 0.08, 0.50, 1, 2, 4 or 12 hours post TK-112690 injection were determined by HPLC using UV detection. Plasma concentrations of TK-112690 increased with increasing doses of TK-112690 administered ip. An increase in plasma uridine was noted almost immediately following administration of TK-112690. At 0.5 hour post TK-112690 dose, a 100 µg/mL plasma concentration TK-112690 is associated with a plasma uridine concentration of approximately 2 µg/mL of uridine (baseline uridine concentration approximately 0.5 µg/mL). As expected, inhibition of UPase by TK-112690 results in elevation of plasma uridine.

DEFINITIONS

When describing the compounds, pharmaceutical compositions containing such compounds, and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope.

"Acyl" refers to a radical —C(O)R, where R is hydrogen, alkyl, cycloalkyl, heterocycloalkyl, aryl, arylalkyl, heteroalkyl, or heteroaryl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, heterocycloalkyl, aryl, arylalkyl, heteroalkyl, heteroaryl, heteroarylalkyl and R is hydrogen, alkyl, alkoxy, cycloalkyl, heterocycloalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)H, —OC(O)-alkyl, —OC(O)-aryl or —OC(O)— cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkynyl and alkynylene. Aliphatic groups typically have from 1 or 2 to 6 or 12 carbon atoms.

"Alkenyl" refers to monovalent olefinically unsaturated hydrocarbyl groups having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkoxy" refers to the group —O-alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(O)-alkoxy where alkoxy is as defined herein.

"Alkoxycarbonylamino" refers to the group —NRC(O) OR' where R is hydrogen, alkyl, aryl or cycloalkyl, and R' is alkyl or cycloalkyl.

"Alkyl" refers to monovalent saturated aliphatic hydrocarbyl groups particularly having up to about 12 or 18 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "alkyl" also includes "cycloalkyls" as defined herein.

"Alkylene" refers to divalent saturated aliphatic hydrocarbyl groups particularly having up to about 12 or 18 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkynyl" refers to acetylenically unsaturated hydrocarbyl groups particularly having up to about 12 or 18 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Amino" refers to the radical —NH$_2$.

"Amino acid" refers to any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine).

"Aminocarbonyl" refers to the group —C(O)NRR where each R is independently hydrogen, alkyl, aryl or cycloalkyl, or where the R groups are joined to form an alkylene group.

"Aminocarbonylamino" refers to the group —NRC(O) NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalkyl, or where the R groups are joined to form an alkylene group.

"Amino-containing saccharide group" refers to a saccharide group having an amino substituent. Representative amino-containing saccharide include L-vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine and the like.

"Aralkyl" or "arylalkyl" refers to an alkyl group, as defined above, substituted with one or more aryl groups, as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Aryloxy" refers to —O-aryl groups wherein "aryl" is as defined herein.

"Autoimmune disease" or "autoimmune condition" refers an illness that occurs when the body tissues are attacked by its own immune system. Examples of autoimuune disease or conditions include multiple sclerosis, ankylosing spondylitis, Crohn's disease, arthritis, psoriasis, Behcet's disease and psoriatic arthritis.

Azido" refers to the radical —$N_3$.

"Carbohydrate" means a mono-, di-, tri-, or polysaccharide, wherein the polysaccharide can have a molecular weight of up to about 20,000, for example, hydroxypropyl-methylcellulose or chitosan. "Carbohydrate" also encompasses oxidized, reduced or substituted saccharide monoradical covalently attached to the anhydropyrimidine (e.g., anhydrothymidine or anhydrouridine), or derivative thereof any atom of the saccharide moiety, e.g., via the aglycone carbon atom. The "mono-, di-, tri-, or polysaccharide" can also include amino-containing saccharide groups. Representative "carbohydrate" include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose-, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units. The saccharides can be either in their open, r pyranose or furanose forms.

"Carboxyl" refers to the radical —C(O)OH.

"Cyano" refers to the radical —CN.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like. "Heterocycloalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl.

"Halo" or "halogen" refers to fluoro, chloro, bromo and iodo. Halo groups can be either fluoro or chloro.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, e.g., heterocycloalkenyl, cycloheteroalkenyl, e.g., heterocycloheteroalkenyl and the like having from 1 to 5, and particularly from 1 to 3 heteroatoms. A heteroatom is any atom other than carbon or hydrogen and is typically, but not exclusively, nitrogen, oxygen, sulfur, phosphorus, boron, chlorine, bromine, or iodine. An unsubstituted heteroatom refers to a pendant heteroatom such as an amine, hydroxyl and thiol. A substituted heteroatom refers to a heteroatom that is other than a pendant heteroatom.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. The heteroaryl group can be a 5-20 membered heteroaryl, or 5-10 membered heteroaryl. Particlar heteroaryl groups are those derived from thiophen, pyrrole, benzothiophene, benzofuran, indole, pyridine, quinoline, imidazole, oxazole and pyrazine.

"Hydroxyl" refers to the radical —OH.

"Nitro" refers to the radical —$NO_2$.

"Peptide" refers to a polyamino acid containing up to 2, 5, 10, or about 100 amino acid residues.

"Polypeptide" means polyamino acid containing from about 100 amino acid units to about 1,000 amino acid units, from about 100 amino acid units to about 750 amino acid units, or from about 100 amino acid units to about 500 amino acid units.

"Proliferative disease" or "proliferative condition" refers to a disease or condition featuring pathologic growth as an underlying pathology. Examples include cancer, arthritis and psoriasis.

"Side-effect" means an undesirable adverse consequence of drug administration such as mucositis associated with administration of methotrexate.

"Stereoisomer" as it relates to a given compound is well understood in the art, and refers to another compound having the same molecular formula, wherein the atoms making up the other compound differ in the way they are oriented in space, but wherein the atoms in the other compound are like the atoms in the given compound with respect to which atoms are joined to which other atoms (e.g. an enantiomer, a diastereomer, or a geometric isomer). See for example, Morrison and Boyd, Organic Chemistry, 1983, 4th ed., Allyn and Bacon, Inc., Boston, Mass., p. 123.

"Substituted" refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, aralkyl, azido, carboxyl, cyano, cycloalkyl, substituted cycloalkyl, halogen, hydroxyl, imidate, keto, nitro, thioalkoxy, substituted thioalkoxy, thioaryloxy, thioketo, thiol, alkylthio, (substituted alkyl)thio, arylthio, (substituted aryl) thio, alkyl-S(O)—, aryl-S(O)—, alkyl-S$(O)_2$— and aryl-S $(O)_2$. Typical substituents include, but are not limited to, —X, —$R^8$ (with the proviso that $R^8$ is not hydrogen), —O—, =O, —$OR^8$, —$SR^8$, —$S^-$, =S, —$NR^8R^9$, =$NR^8$, —$CX_3$, —$CF_3$, —CN, —OCN, —SCN, —NO, —$NO_2$, =$N_2$, —$N_3$, —$S(O)_2$—, —$S(O)_2OH$, —$S(O)_2R^8$, —$OS(O_2)O^-$, —$OS(O)_2R^8$, —$P(O)(O^-)_2$, —$P(O)(OR^8)(O)$, —$OP(O)(OR^8)$ $(OR^9)$, —$C(O)R^8$, —$C(S)R^8$, —$C(O)OR^8$, —$C(O)NR^8R^9$, —$C(O)O^-$, —$C(S)OR^8$, —$NR^{10}OC(O)NR^8R^9$, —$NR^{10}C(S)$ $NR^8R^9$, —$NR^{11}C(NR^{10})NR^8R^9$ and —$C(NR^{10})NR^8R^9$, where each X is independently a halogen.

"Substituted amino" includes those groups recited in the definition of "substituted" herein, and particularly refers to the group —$N(R)_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group.

"Thioalkoxy" refers to the group —S-alkyl.

"Thioaryloxy" refers to the group —S-aryl.

"Thioketo" refers to the group =S.

"Thiol" refers to the group —SH.

"Uridine phosphorylase" refers in enzymology to a phosphorylase (EC 2.4.2.3) that catalyzes the chemical reaction: uridine+phosphate→uracil+alpha-D-ribose 1-phosphate. The two substrates of this enzyme are uridine and phosphate, whereas its two products are uracil and alpha-D-ribose 1-phosphate. This enzyme belongs to the family of glycosyltransferases, specifically the pentosyltransferases. The systematic name of this enzyme class is uridine:phosphate alpha-D-ribosyltransferase. Other names in common use include pyrimidine phosphorylase, UrdPase, UPH, and UPase. This enzyme participates in pyrimidine metabolism.

One having ordinary skill in the art will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

DETAILED DESCRIPTION

Methods of using adjuvants to reduce the toxicity of methotrexate (MTX) in a host are provided. In the subject methods, an effective amount of an MTX active agent is administered to the host in conjunction with the administration of an MTX toxicity-reducing adjuvant of the present invention, where the MTX active agent and MTX toxicity-reducing adjuvant may be administered either sequentially, in any order, simultaneously, or a combination thereof. Also provided are compositions for use in practicing the subject methods, e.g., MTX pharmaceutical compositions having reduced toxicity and kits that include the same. The subject methods and compositions find use in a variety of different applications, including the treatment of a variety of different disease conditions.

Of particular interest is the use of anhydronucleosides as adjuvants to ameliorate the toxic side-effects of MTX, as well as compositions for practicing the subject methods and other applications. Anhydronucleosides are analogs of natural nucleosides, often finding use as intermediates in the synthesis of nucleoside derivatives. They are characterized by having, in addition to the N-glycoside linkage, a covalent linkage either directly or via bridging atoms between the 2', 3', or 5' carbons of the sugar and a carbon, oxygen or nitrogen atom (other than the nitrogen of the glycoside bond) of the base. The anhydropyrimidines are characterized by a pyrimidine base that is covalently linked either directly or via bridging atoms between the 2', 3', or 5' carbons of the sugar and a carbon, oxygen or nitrogen atom (other than the nitrogen of the glycoside bond) of the pyrimidine base. The MTX toxicity-reducing adjuvant 2,2'-anhydropyrimidine and derivatives thereof are of specific interest.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

Any recited method can be carried out in the order of events recited or in any other order which is logically possible.

In further describing the subject invention, the subject methods are described first in greater detail, followed by a review of the various compositions, e.g., formulations and kits, that may find use in the subject methods, as well as a discussion of various representative applications in which the subject methods and compositions find use.

Methods

As summarized above, the subject invention provides methods of administering an MTX active agent to a subject in need thereof, e.g., for the treatment of a host suffering from disease or condition treatable by an MTX active agent (as described in greater detail below). An aspect of the subject methods is that the MTX active agent is administered to the subject in combination with a MTX toxicity-reducing adjuvant. In certain embodiments, the MTX toxicity-reducing adjuvant is a 2,2'-anhydropyrimidine, such as a 2,2'-anhydrouridine or analogue/derivative thereof. By "in combination with", is meant that an amount of the MTX toxicity-reducing adjuvant is administered anywhere from simultaneously to up to 5 hours or more, e.g., 10 hours, 15 hours, 20 hours or more, prior to, or after, the MTX active agent. In certain embodiments, the MTX active agent and MTX toxicity reducing adjuvant are administered sequentially, e.g., where the MTX active agent is administered before or after the MTX toxicity-reducing adjuvant. In yet other embodiments, the MTX active agent and MTX toxicity-reducing adjuvant are administered simultaneously, e.g., where the MTX active agent and MTX toxicity-reducing adjuvant are administered at the same time as two separate formulations, or are combined into a single composition, that is administered to the subject. Regardless of whether the MTX active agent and MTX toxicity-reducing adjuvant are administered sequentially or simultaneously, as illustrated above, or any effective variation thereof, the agents are considered to be administered together or in combination for purposes of the present invention. Routes of administration of the two agents may vary, where representative routes of administration are described in greater detail below.

In the subject methods, an effective amount of an MTX active agent is administered to a host in need thereof in combination with an effective amount of an MTX toxicity-reducing adjuvant. By "MTX active agent" is meant methotrexate or an analogue/derivative thereof. MTX and analogues/derivatives thereof which may be present in the subject compositions include, but are not limited to, those compounds described in U.S. Pat. Nos. 2,512,572; 3,892,801; 3,989,703; 4,057,548; 4,067,867; 4,079,056; 4,080,325; 4,136,101; 4,224,446; 4,306,064; 4,374,987; 4,421,913; 4,767,859; 3,981,983; 4,043,759; 4,093,607; 4,279,992; 4,376,767; 4,401,592; 4,489,065; 4,622,218; 4,625,014; 4,638,045; 4,671,958; 4,699,784; 4,785,080; 4,816,395; 4,886,780; 4,918,165; 4,925,662; 4,939,240; 4,983,586; 4,997,913; 5,024,998; 5,028,697; 5,030,719; 5,057,313; 5,059,413; 5,082,928; 5,106,950; 5,108,987; 4,106,488; 4,558,690; 4,662,359; 4,396,601; 4,497,796; 5,043,270; 5,166,149; 5,292,731; 5,354,753; 5,382,582; 5,698,556; 5,728,692; and 5,958,928; the disclosures of which are herein incorporated by reference.

MTX active agents of the present invention include MTX and any analogues/derivatives thereof whose toxicity is reduced when administered in conjunction with a toxicity-reducing adjuvant according to the subject invention. Whether or not a given MTX active agent is suitable for use according to the present invention can be readily determined using assays employed in the experimental section, below.

Generally, an MTX active agent is suitable for use in the subject methods if its toxicity is reduced by 2 to 10-fold or more, such as by 50-fold or more and sometimes by 100-fold or more, by the MTX toxicity-reducing adjuvant as determined using the *Drosophila melanogaster* assay described in the Experimental section, below. In certain embodiments, the MTX active agent is one whose occurrence and/or intensity of observable toxic side-effects are reduced by the MTX toxicity-reducing adjuvant as observed in the mouse assay described in the experimental section below.

The phrase "MTX toxicity-reducing adjuvant" refers to an agent that reduces toxicity of an MTX active agent. MTX toxicity-reducing adjuvants of interest are those agents that reduce the toxicity of an MTX active agent by 2 to 10-fold or more, such as by 50-fold or more and including by 100-fold or more, as determined using the *Drosophila melanogaster* assay described in the Experimental section, below. In certain embodiments, the MTX toxicity-reducing adjuvants of interest are those that reduce the occurrence and/or intensity of observable toxic side-effects of a given MTX active agent, as observed in the mouse assay described in the Experimental section below. Aspects of toxicity-reducing adjuvants according to certain embodiments of the invention are that the adjuvants do not substantially reduce, and in certain embodiments have no impact at all, on the cytotoxicity of the MTX active agent, e.g., as determined using the protocol described in the Experimental Section below.

The MTX toxicity-reducing adjuvants of interest are 2,2'-anhydropyrimidines and derivatives thereof. In some embodiments, the 2,2'-anhydropyrimidine or derivative thereof is a compound of formula (I):

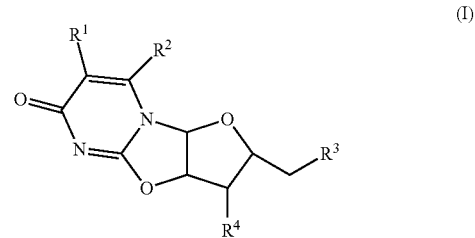

or the pharmaceutically acceptable salts, solvates, hydrates, and prodrug forms thereof, and stereoisomers thereof;

wherein:

each $R^1$, $R^2$, $R^3$ and $R^4$ is independently selected from the group consisting of hydrogen, substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, hydroxyl, halogen, azido, amino, substituted amino, carbohydrate, nucleic acid, amino acid, peptide, dye, fluorophore and polypeptide.

In certain embodiments, the compound is of formula (I), $R^1$, $R^2$, $R^3$ and $R^4$ are independently hydrogen, hydroxyl, heteroatom, $C_1$-$C_{18}$ alkyl, $C_1$-$C_{18}$ substituted alkyl, $C_1$-$C_{18}$ alkenyl, $C_1$-$C_{18}$ acyl, amino, substituted amino, wherein the alkyl, alkenyl or acyl is linear or branched, and optionally substituted with a hydroxyl, an ester and its derivatives, a carboxyl and its derivatives, a cycloalkyl, a heterocycloalkyl, an aryl, a heteroaryl, an aralkyl, a heteroatom, and possibly containing in chain or bridging heteroatoms such as nitrogen, oxygen and sulfur.

Examples of $R^1$ constituents of interest include, but are not limited to: hydrogen; hydroxyl; sulfyhydryl; halogen such as fluorine, chlorine, bromine or iodine, as well as pseudohalogen such as a lower alkylsulfonyl group of 1 to 5 carbons such as methyl-, ethyl-, propyl-, isopropyl-, butyl-, isobutyl-, tert-butyl-, and pentasulfonyl or arylsulfonyl such as benzene, p-toluene, p-nitrobenzenesulfonyl groups; lower alkyl containing 1 to 20 carbons such as methyl, ethyl, propyl, isopropyl, butyl, isobutyl, tert-butyl, pentyl and the like, including substituted lower alkyl such as aminomethyl, hydroxymethyl, methoxy, ethyloxy, propyloxy, benzyloxy, imidate, alkylthio, (substituted alkyl)thio, arylthio, (substituted aryl)thio and the like; lower alkenyl containing 1 to 20 carbons such as vinyl and substituted vinyl, ethynyl and substituted ethynyl, where the substituted vinyl or substituted ethynyl designates substitution of the β position of vinyl or ethynyl by a halogen such as bromine, chlorine, fluorine or iodine, or substitution by an alkyl of 1 to 5 carbon atoms such as methyl, ethyl, propyl, butyl, pentyl and the like, or aralkyl such as benzyl, p-chlorobenzyl, p-nitrobenzyl and the like, or aryl such as phenyl, p-nitrophenyl, p-tolyl, p-anisyl, naphtyl and the like; lower alkanoyl (acyl groups) containing 1 to 20 carbons such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonyl and the like; lower aryl containing 1 to 20 carbons such as phenyl, p-tolyl, p-chlorophenyl, p-aminophenyl, p-nitrophenyl, p-anisyl and the like; lower aroyl containing 1 to 20 carbons such as benzoyl and naphthoyl, where the aromatic group may be additionally substituted by alkyl, alkoxy, halo, or nitro moieties such as p-tolnoyl, p-anisoyl, p-chlorobenzoyl, p-nitrobenzoyl or 2,4-dinitrobenzoyl, pentafluorobenzoyl and the like, or another aroyl such as benzyloxybenzoyl and the like; lower aralkyl containing 1 to 20 carbons such as benzyl, benzhydryl, p-chlorobenzyl, m-chlorobenzyl, p-nitrobenzyl, benzyloxybenzyl, pentafluorobenzyl and the like; amino or alkylamino containing 1 to 20 carbons such as a monoalkyl- or monoaralkylamino groups like methylamino, ethylamino, propylamino or benzylamino and the like, dialkylamino such as dimethylamino, diethylamino, dibenzylamino, pyrrolidino, piperidino or molpholino and the like.

Thus in certain embodiments, $R^1$ is hydrogen, hydroxyl, sulfyhydryl, amino, substituted amino, hydroxymethyl, monomethoxy, halogen, pseudohalogen, or a lower hydrocarbon (which hydrocarbon can be substituted or unsubstituted) containing from 1 to 20 atoms. In a particular embodiment, $R^1$ is a lower hydrocarbon selected from alkyl, substituted alkyl, alkenyl, alkanoyl, aryl, aroyl, aralkyl, or alkylamino. In a particular embodiment, $R^1$ is a lower hydrocarbon substituted with alkoxy, substituted alkoxy, imidate, arylthio, or (substituted aryl)thio. In other embodiments, $R^1$ is a lower alkyl selected from methyl, ethyl, propyl, isopropyl, butyl, isobutyl, tert-butyl and pentyl. In other embodiments, $R^1$ is a lower alkenyl selected from vinyl, substituted vinyl, ethynyl, or substituted ethynyl. In other embodiments, $R^1$ is a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonyl. In other embodiments, $R^1$ is lower aryl selected from phenyl, p-tolyl, p-chlorophenyl, p-aminophenyl, p-nitrophenyl, p-anisyl. In yet other embodiments, $R^1$ is a lower aroyl selected from benzoyl and naphthoyl. In other embodiments, $R^1$ is a lower aralkyl selected from benzyl, benzhydryl, p-chlorobenzyl, m-chlorobenzyl, p-nitrobenzyl, benzyloxybenzyl, or pentafluorobenzyl. In certain other embodiments, $R^1$ is a lower alkylamino is selected from monoalkylamino, monoaralkylamino, dialkylamino, diaralkylamino, and benzylamino.

Compounds of interest include, but are not limited to, those of formula (I) where $R^1$ is selected from hydrogen, fluorine, trifluoromethyl, methyl, ethyl, propyl, butyl, isopropyl, isobutyl, acetyl, propionyl, butyryl, 2-bromovinyl, phenyl, benzyl, benzoyl, benzyloxybenzyl, benzylamino, alkyloxyalkyl, benzyloxyalkyl, imidatealkyl, arylthio, and (substituted aryl)thio. Thus in certain embodiments, the compound is of formula (I), and $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, $Br-CH=CH$, phenyl, benzyl, benzoyl, benzyloxybenzyl, benzyl-NH—, $CH_3CH_2OCH_2$, benzyl-O—$CH_2$, $CH_3OCH_2$, $CH_3C(NH)$—O—$CH_2$, or $CH_3$-phenyl-O—$CH_2$.

Examples of $R^2$ constituents of interest include, but are not limited to: hydrogen; hydroxyl; sulfyhydryl; halogen such as fluorine, chlorine, bromine or iodine, as well as pseudohalogen such as a lower alkylsulfonyl group of 1 to 5 carbons such as methyl-, ethyl-, propyl-, isopropyl-, butyl-, isobutyl-, tert-butyl-, and pentasulfonyl or arylsulfonyl such as benzene, p-toluene, p-nitrobenzenesulfonyl groups; lower alkyl containing 1 to 20 carbons such as methyl, ethyl, propyl, isopropyl, butyl, isobutyl, tert-butyl, pentyl and the like, including substituted lower alkyl such as aminomethyl, hydroxymethyl, methoxy, ethyloxy, propyloxy, and the like; lower alkenyl containing 1 to 20 carbons such as vinyl and substituted vinyl, ethynyl and substituted ethynyl, where the substituted vinyl or substituted ethynyl designates substitution of the β position of vinyl or ethynyl by a halogen such as bromine, chlorine, fluorine or iodine, or substitution by an alkyl of 1 to 5 carbon atoms such as methyl, ethyl, propyl, butyl, pentyl and the like, or aralkyl such as benzyl, p-chlorobenzyl, p-nitrobenzyl and the like, or aryl such as phenyl, p-nitrophenyl, p-tolyl, p-anisyl, naphtyl and the like; lower alkanoyl (acyl groups) and esters thereof of a main chain containing 1 to 20 carbons such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonyl and the like; lower aryl containing 1 to 20 carbons such as phenyl, p-tolyl, p-chlorophenyl, p-aminophenyl, p-nitrophenyl, p-anisyl and the like; lower aroyl containing 1 to 20 carbons such as benzoyl and naphthoyl, where the aromatic group may be additionally substituted by alkyl, alkoxy, halo, or nitro moieties such as p-tolnoyl, p-anisoyl, p-chlorobenzoyl, p-nitrobenzoyl or 2,4-dinitrobenzoyl, pentafluorobenzoyl and the like, or another aroyl such as benzyloxybenzoyl and the like; lower aralkyl containing 1 to 20 carbons such as benzyl, benzhydryl, p-chlorobenzyl, m-chlorobenzyl, p-nitrobenzyl, benzyloxybenzyl, pentafluorobenzyl and the like; lower aryloxy containing 1 to 20 carbons such as phenyloxy (i.e., O-phenyl), benzyloxy (i.e., O-benzyl), benzhydryloxy (i.e., O-benzylhydryl), p-chlorobenzyloxy (i.e., O-(p-chlorobenzyl)), m-chlorobenzyloxy (i.e., O-(m-chlorobenzyl)), p-nitrobenzyloxy (i.e., O-(p-nitrobenzyl)), (4-benzyloxybenzyl)-oxy (i.e., O-benzyloxybenzyl), or pentafluorobenzyloxy (i.e., O-pentafluorobenzyl); esters of aryloxys, such as lower aroyloxy (i.e., O-aroyl) containing 1 to 20 carbons such as benzoyloxy (i.e., O-benzoyl), diphenylacetyloxy (i.e., O-diphenylacetyl), p-chlorobenzoyloxy (i.e., O-(p-chlorobenzoyl)), m-chlorobenzoyloxy (i.e., O-(m-chlorobenzoyl)), p-nitrobenzoyloxy (i.e., O-(p-nitrobenzoyl)), (4-benzyloxybenzoyl)-oxy (i.e., O-benzyloxybenzoyl), or pentafluorobenzoyloxy (i.e., O-pentafluorobenzoyl); amino or alkylamino containing 1 to 20 carbons such as a monoalkyl- or monoaralkylamino groups like methylamino, ethylamino, propylamino or benzylamino and the like, dialkylamino such as dimethylamino, diethylamino, dibenzylamino, pyrrolidino, piperidino or molpholino and the like.

Thus in certain embodiments, $R^2$ is hydrogen, hydroxyl, sulfyhydryl, amino, hydroxymethyl, monomethoxy, halogen, pseudohalogen, or a lower hydrocarbon (which hydrocarbon can be substituted or unsubstituted) containing from 1 to 20 atoms, and esters thereof. In a particular embodiment, $R^2$ is a lower hydrocarbon selected from alkyl, alkenyl, alkanoyl, aryl, aroyl, aryloxy, aroyloxy, aralkyl, or alkylamino. In other embodiments, $R^2$ is a lower alkyl selected from methyl, ethyl, propyl, isopropyl, butyl, isobutyl, tert-butyl and pentyl. In other embodiments, $R^2$ is a lower alkenyl selected from vinyl, substituted vinyl, ethynyl, or substituted ethynyl. In other embodiments, $R^2$ is a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonyl. In other embodiments, $R^2$ is lower aryl selected from phenyl, p-tolyl, p-chlorophenyl, p-aminophenyl, p-nitrophenyl, p-anisyl. In yet other embodiments, $R^2$ is a lower aroyl selected from benzoyl and naphthoyl. In other embodiments, $R^2$ is a lower aralkyl selected from benzyl, benzhydryl, p-chlorobenzyl, m-chlorobenzyl, p-nitrobenzyl, benzyloxybenzyl, or pentafluorobenzyl. In other embodiments, $R^2$ is a lower aryloxy selected from phenyloxy, benzyloxy, benzhydryloxy, p-chlorobenzyloxy, m-chlorobenzyloxy, p-nitrobenzyloxy, (4-benzyloxybenzyl)-oxy, or pentafluorobenzyloxy. In other embodiments, $R^2$ is a lower aroyloxy selected from benzoyloxy, diphenylacetyloxy, p-chlorobenzoyloxy, m-chlorobenzoyloxy, p-nitrobenzoyloxy, (4-benzyloxybenzoyl)-oxy, or pentafluorobenzoyloxy. In certain other embodiments, $R^2$ is a lower alkylamino is selected from monoalkylamino, monoaralkylamino, dialkylamino, and diaralkylamino. Thus in certain embodiments, $R^2$ can not only be hydrogen or hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O.

Compounds of interest include, but are not limited to, those of formula (I) where $R^2$ is selected from hydrogen, fluorine, trifluoromethyl, methyl, ethyl, propyl, butyl, isopropyl, isobutyl, acetyl, propionyl, butyryl, 2-bromovinyl, phenyl, phenyloxy, benzyl, benzoyl, benzoyloxy and benzyloxybenzyl. Thus in certain embodiments, the compound is of formula (I), and $R^2$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzoyl, benzoyloxy, or benzyloxybenzyl.

In specific embodiments of interest, the compound is of formula (I), and $R^2$ is hydrogen, hydroxyl, or an O-linked substituent. This includes compounds of formula (I), where $R^2$ is H, OH or $C_6H_5C(O)O$.

Examples of $R^3$ of interest include, but are not limited to: hydrogen; hydroxyl; azido; sulfyhydryl; halogen; pseudohalogen; lower alkyl containing 1 to 20 carbons such as methyl, ethyl, propyl, isopropyl, butyl, isobutyl, tert-butyl, pentyl and the like, including a substituted lower alkyl such as aminomethyl, hydroxymethyl, methoxy, ethyloxy, propyloxy, and the like; lower alkanoyl (acyl) including esters thereof of a main chain of 1 to 20 carbon atoms such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonyl and the like; lower aryl such as phenyl, p-nitrophenyl, p-tolyl, p-anisyl, naphtyl and the like; lower aroyl (acyl radical of an aromatic acid) of 1 to 20 carbons such as benzoyl and naphthoyl, where the aromatic group may be additionally substituted by alkyl, alkoxy, halo, or nitro moieties such as p-tolnoyl, p-anisoyl, p-chlorobenzoyl, p-nitrobenzoyl or 2,4-dinitrobenzoyl, pentafluorobenzoyl and the like; lower aryloxy of 1 to 20 carbons such as phenyloxy, benzyloxy, benzhydryloxy, p-chlorobenzyloxy, m-chlorobenzyloxy, p-nitrobenzyloxy, (4-benzyloxybenzyl)-oxy, or pentafluorobenzyloxy and the like; as well as esters of aryloxys, such as lower aroyloxy (O-aroyls) of 1 to 20 carbons such as benzoyloxy, diphenylacetyloxy, p-chlorobenzoyloxy, m-chlorobenzoyloxy, p-nitrobenzoyloxy, (4-benzyloxybenzoyl)-oxy, or pentafluorobenzoyloxy and the like. $R^3$ may also be adamantoyl, or substituted adamantoyl.

Thus in certain embodiments, $R^3$ is hydrogen, hydroxyl, azido, sulfyhydryl, hydroxymethyl, halogen, or pseudohalogen. In other embodiments, $R^3$ is a lower hydrocarbon selected from alkyl, alkanoyl, aryl, aroyl, aryloxy, aroyloxy, or aralkyl. In other embodiments, $R^3$ is a lower alkyl selected from methyl, ethyl, propyl, isopropyl, butyl, isobutyl, tert-butyl and pentyl. In other embodiments, $R^3$ is a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonyl. In other embodiments, $R^3$ is a lower aryl selected from phenyl, p-tolyl, p-chlorophenyl, p-aminophenyl, p-nitrophenyl, p-anisyl and the like. In other embodiments, $R^3$ is a lower aroyl selected from benzoyl and naphthoyl. In yet other certain embodiments, $R^3$ is a lower aralkyl selected from benzyl, benzhydryl, p-chlorobenzyl, m-chlorobenzyl, p-nitrobenzyl, benzyloxybenzyl, or pentafluorobenzyl. In other embodiments, $R^3$ is a lower aryloxy selected from phenyloxy, benzyloxy, benzhydryloxy, p-chlorobenzyloxy, m-chlorobenzyloxy, p-nitrobenzyloxy, (4-benzyloxybenzyl)-oxy, or pentafluorobenzyloxy. In other embodiments, $R^3$ is a lower aroyloxy selected from benzoyloxy, diphenylacetyloxy, p-chlorobenzoyloxy, m-chlorobenzoyloxy, p-nitrobenzoyloxy, (4-benzyloxybenzoyl)-oxy, or pentafluorobenzoyloxy. Thus in certain embodiments, $R^3$ can not only be hydrogen or hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O.

Compounds of interest are those of formula (I) where $R^3$ is hydrogen, hydroxyl, halogen, azido, or an O-linked substituent. This includes compounds of formula (I) where $R^3$ is selected from hydrogen, hydroxyl, n-butoxy, isobutyloxy, t-butyloxy, phenyloxy, benzyloxy, benzoyloxy, and pentafluorobenzoyloxy. Thus in certain embodiments, the compound is of formula (I), and $R^3$ is selected from H, OH, $CH_3CH_2CH_2CH_2O$, $(CH_3)_2CH_2CH_2O$, $(CH_3)_3CO$, $C_6H_5O$, benzoyloxy, and pentafluorobenzoyloxy.

In specific embodiments of interest, the compound is of formula (I), where $R^3$ is H, OH, F, Cl, Br, I, $N_3$, or $C_6H_5C(O)O$. Of special interest is a compound of formula (I), where $R^3$ is OH, or O-acyl (for example, an ester such as $C_6H_5C(O)O$).

Examples of $R^4$ include, but are not limited to: hydrogen; hydroxyl; sulfhydryl; halogen such as fluorine, chlorine, bromine or iodine; amino or lower alkylamino. $R^4$ also is exemplified by lower alkyl, with acyl groups which may be lower alkanoyl groups of 1 to 7 carbon atoms such as formyl, acetyl, propionyl, isopropionyl, butyryl, isobutyryl, tert-butyryl and the like, and esters thereof. Thus, $R^4$ can also be aroyl (and esters thereof such as O-linked aroyls, i.e., O-arolys or arolyoxy) such as benzoyl and naphthoyl wherein the aromatic group may be additionally substituted by alkyl, alkoxy, halo, or nitro moieties such as p-tolnoyl, p-anisoyl, p-chlorobenzoyl, p-nitrobenzoyl or 2,4-dinitrobenzoyl and the like. Accordingly, in certain embodiments, $R^4$ can not only be hydrogen or hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the O.

Thus in certain embodiments, $R^4$ is hydrogen; hydroxyl; sulfhydryl; halogen, amino aminomethyl, or aminodimethyl. In other embodiments, $R^4$ is a lower alkyl, acyl, aroyl, or aroyloxy. This includes a specific embodiment, where the compound of formula (I) is one where $R^4$ is hydrogen, flourine, hydroxyl, amino, aminomethyl, aminodimethyl, t-butyloxy, phenyloxy or benzoyloxy (for example, a compound of formula (I), where $R^4$ is H, F, OH, $NH_2$, $NHCH_3$, $N(CH_3)_2$, $(CH_3)_3CO$, $C_6H_5O$ or $C_6H_5C(O)O$).

Compounds of particular interest are those of formula (I) where $R^4$ is hydrogen, hydroxyl, or an O-linked substituent. In specific embodiments, the compound is of formula (I), where $R^4$ is H, OH or $C_6H_5C(O)O$. Of special interest is a compound of formula (I), where $R^4$ is OH, or O-acyl (for example, an ester such as $C_6H_5C(O)O$).

Of interest are compounds of formula (I) where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzoyl, benzoyloxy, or benzyloxybenzyl, and where $R^3$ and $R^4$ are each hydroxyl. These include the compounds: 2,2'-anhydrouridine; 2,2'-anhydro-5-fluorouridine; 2,2'-anhydro-5-trifluoromethyluridine; 2,2'-anhydro-5-methyluridine; 2,2'-anhydro-5-ethyluridine; 2,2'-anhydro-5-propyluridine; 2,2'-anhydro-5-isopropyluridine; 2,2'-anhydro-5-isobutyluridine; 2,2'-anhydro-5-methylacyluridine; 2,2'-anhydro-5-propylacyluridine; 2,2'-anhydro-5-(2-bromovinyl)-uridine; 2,2'-anhydro-5-phenylluridine; 2,2'-anhydro-5-benzyluridine; 2,2'-anhydro-5-benzyouridine; and 2,2'-anhydro-5-(benzyloxybenzyl)-uridine. Of special interest is 2,2'-anhydro-5-methyluridine, or the pharmaceutically acceptable salts, solvates, hydrates, and prodrug forms thereof, and stereoisomers thereof.

Additional compounds of interest are compounds of formula (I) where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzyloxy, benzoyl, benzoyloxy, or benzyloxybenzyl, and where $R^3$ is hydroxyl, and $R^4$ is benzoyloxy. These include the compounds: 3'-O-benzoyl-2,2'-anhydrouridine; 3'-O-benzoyl-2,2'-anhydro-5-fluorouridine; 3'-O-benzoyl-2,2'-anhydro-5-trifluoromethyluridine; 3'-O-benzoyl-2,2'-anhydro-5-methyluridine; 3'-O-benzoyl-2,2'-anhydro-5-ethyluridine; 3'-O-benzoyl-2,2'-anhydro-5-propyluridine; 3'-O-benzoyl-2,2'-anhydro-5-isopropyluridine; 3'-β-benzoyl-2,2'-O-anhydro-5-isobutyluridine; 3'-O-benzoyl-2,2'-anhydro-5-methylacyluridine; 3'-O-benzoyl-2,2'-anhydro-5-propylacyluridine; 3'-β-benzoyl-2,2'-anhydro-5-(2-bromovinyl)-uridine; 3'-O-benzoyl-2,2'-anhydro-5-phenylluridine; 3'-O-benzoyl-2,2'-anhydro-5-benzyluridine; 3'-O-benzoyl-2,2'-anhydro-5-benzyouridine; and 3'-O-benzoyl-2,2'-anhydro-5-(benzyloxybenzyl)-uridine. Of specific interest is 3'-O-benzoyl-2,2'-anhydro-5-methyluridine, or the pharmaceutically acceptable salts, solvates, hydrates, and prodrug forms thereof, and stereoisomers thereof.

Also of interest are compounds of formula (I) where: $R^1$ is H, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2CH$, $(CH_3)_2CH_2CH_2$, $CH_3(O)CCH_2$, $CH_3(O)CCH_2CH_2$, Br—CH=CH, phenyl, phenyloxy, benzyl, benzyloxy, benzoyl, benzoyloxy, or benzyloxybenzyl, and where $R^3$ is benzoyloxy, and $R^4$ is hydroxyl. These include the compounds: 5'-O-benzoyl-2,2'-anhydrouridine; 5'-O-benzoyl-2,2'-anhydro-5-fluorouridine; 5'-O-benzoyl-2,2'-anhydro-5-trifluoromethyluridine; 5'-O-benzoyl-2,2'-anhydro-5-methyluridine; 5'-O-benzoyl-2,2'-anhydro-5-ethyluridine; 5'-O-benzoyl-2,2'-anhydro-5-propyluridine; 5'-O-benzoyl-2,2'-anhydro-5-isopropyluridine; 5'-O-benzoyl-2,2'-O-anhydro-5-isobutyl uridine; 5'-O-benzoyl-2,2'-anhydro-5-methylacyluridine; 5'-O-benzoyl-2,2'-anhydro-5-propylacyluridine; 5'-O-benzoyl-2,2'-anhydro-5-(2-bromovinyl)-uridine; 5'-O-benzoyl-2,2'-anhydro-5-phenylluridine; 5'-O-benzoyl-2,2'-anhydro-5-benzyluridine; 5'-O-benzoyl-2,2'-anhydro-5-benzyouridine; and 5'-O-benzoyl-2,2'-anhydro-5-(benzyloxybenzyl)-uridine. Of specific interest is 5'-O-benzoyl-2,2'-anhydro-5-methyluridine, or the pharmaceutically acceptable salts, solvates, hydrates, and prodrug forms thereof, and stereoisomers thereof.

The 2,2'-anhydropyrimidine compounds of the invention may be in compositions that contain single stereoisomers, mixtures of stereoisomers, as well various derivatives thereof that can occur as equilibrium mixtures of tautomers. For instance, 2,2'-anhydropyrimidines according to formula (I) include four stereo centers with respect to the furano ring, which includes the α and β anomers, and the L or D mirror image configurations. Examples of stereoisomers of the 2,2'-anhydropyrimidine compounds of the invention are the β-D-isomer, β-L-isomer, α-D-isomer, and α-L-isomer, as well as tautomers and mixtures including α,β-D-isomers, α,β-L-isomers, α-DL-isomers, and β-DL-isomers. Thus in one embodiment, compositions are provided that consists essentially of a stereoisomer of a 2,2'-anhydropyrimidine that is a β-D-isomer, β-L-isomer, α-D-isomer, or an α-L-isomer. Stereoisomers exhibiting improved activity on a molar basis or improved specificity with respect to interfering with MTX efficacy are of special interest.

Stereoisomers of particular interest include: 2,2'-anhydro-1-(β-D-arabinofuranosyl)uracil; 2,2'-anhydro-1-(β-D-arabinofuranosyl)-5-fluorouracil; 2,2'-anhydro-1-(β-D-arabinofuranosyl)-5-trifluoromethyluracil; 2,2'-anhydro-1-(β-D-arabinofuranosyl)-5-methyluracil; 2,2'-anhydro-1-(β-D-arabinofuranosyl)-5-ethyluracil; 2,2'-anhydro-1-(β-D-arabinofuranosyl)-5-n-propyluracil; 2,2'-anhydro-1-(3-D-arabinofuranosyl)-5-isopropyluracil; 2,2'-anhydro-1-(β-D-arabinofuranosyl)-5-isobutyluracil; 2,2'-anhydro-1-(β-D-arabinofuranosyl)-5-methyacyl uracil; 2,2'-anhydro-1-(β-D-arabinofuranosyl)-5-propylacyluracil; 2,2'-anhydro-1-(β-D-arabinofuranosyl)-5-(2-bromovinyl)uracil; 2,2'-anhydro-1-(β-D-arabinofuranosyl)-5-phenyluracil; 2,2'-anhydro-1-(β-D-arabinofuranosyl)-5-benzyluracil; 2,2'-anhydro-1-(β-D-arabinofuranosyl)-5-benzyouracil; and 2,2'-anhydro-1-(β-D-arabinofuranosyl)-5-(3-benzyoxybenzyl)uracil. Further stereoisomers of interest include: 3'-O-benzoyl-2,2'-anhydro-1-(β-D-arabinofuranosyl)uracil; 3'-O-benzoyl-2,2'-anhydro-1-(β-D-arabinofuranosyl)-5-fluororacil; 3'-O-benzoyl-2,2'-anhydro-1-(β-D-arabinofuranosyl)-5- trifluoromethyl uracil; 3'-O-benzoyl-2,2'-anhydro-1-(β-D-arabinofuranosyl)-5-methyl uracil; 3'-O-benzoyl-2,2'-anhydro-1-(β-D-arabinofuranosyl)-5-ethyluracil; 3'-O-benzoyl-2,2'-anhydro-1-(β-D-arabinofuranosyl)-5-n-propyluracil; 3'-β-benzoyl-2,2'-anhydro-1-(β-D-arabinofuranosyl)-5-isopropyluracil; 3'-O-benzoyl-2,2'-anhydro-1-(β-D-arabinofuranosyl)-5-isobutyluracil; 3'-O-benzoyl-2,2'-anhydro-1-(β-D-arabinofuranosyl)-5-methyacyluracil; 3'-O-benzoyl-2,2'-anhydro-1-(β-D-arabinofuranosyl)-5-propylacyluracil; 3'-O-benzoyl-2,2'-anhydro-1-(β-D-arabinofuranosyl)-5-(2-bromovinyl)uracil; 3'-O-benzoyl-2,2'-anhydro-1-(β-D-arabinofuranosyl)-5-phenyluracil; 3'-O-benzoyl-2,2'-anhydro-1-(β-D-arabinofuranosyl)-5-benzyluracil; 3'-O-benzoyl-2,2'-anhydro-1-(β-D-arabinofuranosyl)-5-benzyoluracil; and 3'-O-benzoyl-2,2'-anhydro-1-((3-D-arabinofuranosyl)-5-(3-benzyoxybenzyl)uracil. Additional stereoisomers of interest include: 5'-O-benzoyl-2,2'-anhydro-1-(β-D-arabinofuranosyl)uracil; 5'-O-benzoyl-2,2'-anhydro-1-(β-D-arabinofuranosyl)-5-fluorouracil; 5'-O-benzoyl-2,2'-anhydro-1-(β-D-arabinofuranosyl)-5-trifluoromethyluracil; 5'-O-benzoyl-2,2'-anhydro-1-(β-D-arabinofuranosyl)-5-methyluracil; 5'-O-benzoyl-2,2'-anhydro-1-(β-D-arabinofuranosyl)-5-ethyluracil; 5'-O-benzoyl-2,2'-anhydro-1-(β-D-arabinofuranosyl)-5-n-propyluracil; 5'-O-benzoyl-2,2'-anhydro-1-(β-D-arabinofuranosyl)-5-isopropyluracil; 5'-O-benzoyl-2,2'-anhydro-1-(β-D-arabinofuranosyl)-5-isobutyluracil; 5'-O-benzoyl-2,2'-anhydro-1-(β-D-arabinofuranosyl)-5-methyacyluracil; 5'-O-benzoyl-2,2'-anhydro-1-(β-D-arabinofuranosyl)-5-propylacyluracil; 5'-O-benzoyl-2,2'-anhydro-1-(β-D-arabinofuranosyl)-5-(2-bromovinyl)uracil; 5'-O-benzoyl-2,2'-anhydro-1-(β-D-arabinofuranosyl)-5-phenyluracil; 5'-O-benzoyl-2,2'-anhydro-1-(β-D-arabinofuranosyl)-5-benzyluracil; 5'-O-benzoyl-2,2'-anhydro-1-(β-D-arabinofuranosyl)-5-benzyoluracil; and 5'-O-benzoyl-2,2'-anhydro-1-(β-D-arabinofuranosyl)-5-(3-benzyoxybenzyl)uracil.

Examples of other analogs or derivatives of the 2,2'-anhydropyrimidines of the invention, and stereoisomers thereof include: 3'-O-acetyl-2,2'-anhydro-5-propyluridine (3'-O-acetyl-2,2'-anhydro-1-(β-D-arabinofuranosyl)-5-propyl uracil); and 3'-O-acetyl-2,2'-anhydro-5-isopropyluridine (3'-O-acetyl-2,2'-anhydro-1-(β-D-arabinofuranosyl)-5-isopropyluracil); as well as the 2,2'-anhydrocytidines, and analogs and derivatives thereof, of which the stereoisomer 2,2'-anhydro-1-(β-D-arabinofuranosyl)cytosine is one example.

As noted above, stereoisomers and the various 2,2'-anhydropyrimidines of particular interest are those which exhibit improved activity on a molar basis, or improved specificity with respect to not interfering with MTX efficacy. Such compounds can be readily selected for this purpose by comparing against a matrix of compounds of particular interest, such as those illustrated in Table 1 (where the compound is of formula (I)).

TABLE 1

The compound is of formula (I)

| Compound | Stereoisomer | $R^1$ | $R^2$ | $R^3$ | $R^4$ |
|---|---|---|---|---|---|
| I-a | β-D-isomer | H | H | OH | OH |
| I-b | β-D-isomer | $CH_3$ | H | OH | OH |
| I-c | β-D-isomer | $CH_3CH_2$ | H | OH | OH |
| I-d | β-D-isomer | $CH_3CH_2CH$ | H | OH | OH |
| I-e | β-D-isomer | BrCH=CH | H | OH | OH |
| I-f | β-D-isomer | $C_6H_5CH_2$ | H | OH | OH |

TABLE 1-continued

The compound is of formula (I)

| Compound | Stereoisomer | $R^1$ | $R^2$ | $R^3$ | $R^4$ |
|---|---|---|---|---|---|
| I-g | β-D-isomer | H | H | $C_6H_5C(O)O$ | OH |
| I-h | β-D-isomer | $CH_3$ | H | $C_6H_5C(O)O$ | OH |
| I-i | β-D-isomer | $CH_3CH_2$ | H | $C_6H_5C(O)O$ | OH |
| I-j | β-D-isomer | $CH_3CH_2CH$ | H | $C_6H_5C(O)O$ | OH |
| I-k | β-D-isomer | BrCH=CH | H | $C_6H_5C(O)O$ | OH |
| I-l | β-D-isomer | $C_6H_5CH_2$ | H | $C_6H_5C(O)O$ | OH |
| I-m | β-D-isomer | F—$C_6H_5CH_2$ | H | OH | OH |
| I-n | β-D-isomer | $NO_2$—$C_6H_5CH_2$ | H | OH | OH |
| I-o | β-D-isomer | $NH_2$—$C_6H_5CH_2$ | H | OH | OH |
| I-p | β-D-isomer | Cl—$C_6H_5CH_2$ | H | OH | OH |
| I-q | β-D-isomer | Alkyl-$C_6H_5CH_2$ | H | OH | OH |
| I-r | β-D-isomer | Methoxy-$C_6H_5CH_2$ | H | OH | OH |
| I-s | β-D-isomer | Thiol-$C_6H_5CH_2$ | H | OH | OH |
| I-t | β-D-isomer | F—$C_6H_5CH_2$ | H | $C_6H_5C(O)O$ | OH |
| I-u | β-D-isomer | $NO_2$—$C_6H_5CH_2$ | H | $C_6H_5C(O)O$ | OH |
| I-v | β-D-isomer | $NH_2$—$C_6H_5CH_2$ | H | $C_6H_5C(O)O$ | OH |
| I-w | β-D-isomer | Cl—$C_6H_5CH_2$ | H | $C_6H_5C(O)O$ | OH |
| I-x | β-D-isomer | Alkyl-$C_6H_5CH_2$ | H | $C_6H_5C(O)O$ | OH |
| I-y | β-D-isomer | Methoxy-$C_6H_5CH_2$ | H | $C_6H_5C(O)O$ | OH |
| I-z | β-D-isomer | Thiol-$C_6H_5CH_2$ | H | $C_6H_5C(O)O$ | OH |
| I-a' | β-D-isomer | H | OH | H | OH |
| I-b' | β-D-isomer | $CH_3$ | OH | H | OH |
| I-c' | β-D-isomer | $CH_3CH_2$ | OH | H | OH |
| I-d' | β-D-isomer | $CH_3CH_2CH$ | OH | H | OH |
| I-e' | β-D-isomer | BrCH=CH | OH | H | OH |
| I-f' | β-D-isomer | $C_6H_5CH_2$ | OH | H | OH |
| I-g' | β-D-isomer | H | $C_6H_5C(O)O$ | H | OH |
| I-h' | β-D-isomer | $CH_3$ | $C_6H_5C(O)O$ | H | OH |
| I-i' | β-D-isomer | $CH_3CH_2$ | $C_6H_5C(O)O$ | H | OH |
| I-j' | β-D-isomer | $CH_3CH_2CH$ | $C_6H_5C(O)O$ | H | OH |
| I-k' | β-D-isomer | BrCH=CH | $C_6H_5C(O)O$ | H | OH |
| I-l' | β-D-isomer | $C_6H_5CH_2$ | $C_6H_5C(O)O$ | H | OH |
| I-m' | β-D-isomer | F—$C_6H_5CH_2$ | OH | H | OH |
| I-n' | β-D-isomer | $NO_2$—$C_6H_5CH_2$ | OH | H | OH |
| I-o' | β-D-isomer | $NH_2$—$C_6H_5CH_2$ | OH | H | OH |
| I-p' | β-D-isomer | Cl—$C_6H_5CH_2$ | OH | H | OH |
| I-q' | β-D-isomer | Alkyl-$C_6H_5CH_2$ | OH | H | OH |
| I-r' | β-D-isomer | Methoxy-$C_6H_5CH_2$ | OH | H | OH |
| I-s' | β-D-isomer | Thiol-$C_6H_5CH_2$ | OH | H | OH |
| I-t' | β-D-isomer | F—$C_6H_5CH_2$ | $C_6H_5C(O)O$ | H | OH |
| I-u' | β-D-isomer | $NO_2$—$C_6H_5CH_2$ | $C_6H_5C(O)O$ | H | OH |
| I-v' | β-D-isomer | $NH_2$—$C_6H_5CH_2$ | $C_6H_5C(O)O$ | H | OH |
| I-w' | β-D-isomer | Cl—$C_6H_5CH_2$ | $C_6H_5C(O)O$ | H | OH |
| I-x' | β-D-isomer | Alkyl-$C_6H_5CH_2$ | $C_6H_5C(O)O$ | H | OH |
| I-y' | β-D-isomer | Methoxy-$C_6H_5CH_2$ | $C_6H_5C(O)O$ | H | OH |
| I-z' | β-D-isomer | Thiol-$C_6H_5CH_2$ | $C_6H_5C(O)O$ | H | OH |

As mentioned above, the compounds in Table I are illustrative but not limiting. For example, $R^4$ can be not only hydroxyl, but also an O-acyl, alkoxy, alkoxycarbonyl, alkoxycarbonylamino, O-alkyl, O-alkylene, O-alkynyl, O-aralkyl, O-aryl, O-aryloxy, O-carbohydrate, O-cycloalkenyl, O-cycloalkyl, O-heterocycloalkyl, O-heteroaryl. In addition, an S can substitute for the 0 and other combinations of the structural elements such as described herein, as well as other streochemical orientations, are also possible.

In certain embodiments, acyl derivatives of the 2,2'-anyhydropyrimidines of formula (I) are of interest. Thus, compounds of formula (I) include those in which $R^1$, $R^2$, $R^3$ and $R^4$ are as defined above, wherein at least one of $R^2$, $R^3$ and $R^4$ is an acyl derivative. By "acyl derivative" is intended a derivative of a 2,2'-anyhydropyrimidine of formula (I) in which at least one of $R^2$, $R^3$ and $R^4$ is a substantially nontoxic organic acyl substituent obtainable from a carboxylic acid that is attached to a hydroxyl group on the ribose or pyrimidine ring of formula (I) through an ester linkage.

Acyl derivatives of a 2,2'-anyhydropyrimidine compound of formula (I) include those in which $R^1$ is as defined above, and each $R^2$, $R^3$ and $R^4$ is independently hydrogen, hydroxyl or an acyl radical, with the proviso that at least one of $R^2$, $R^3$ and $R^4$ is not hydrogen. In another embodiment, the acyl derivative of a 2,2'-anyhydropyrimidine is a compound of formula (I) in which $R^1$ and $R^2$ are as defined above, with the proviso that $R^2$ is other than hydrogen, and each $R^3$ and $R^4$ is independently hydroxyl or an acyl radical. In one embodiment, the acyl derivative of a 2,2'-anyhydropyrimidine is a compound of formula (I) in which $R^1$ is as defined above, $R^2$ is hydrogen, and each $R^3$ and $R^4$ is independently hydroxyl or an acyl radical. Of particular interest, is an acyl derivative of a 2,2'-anyhydropyrimidine compound of formula (I), wherein $R^1$ is methyl, $R^2$ is hydrogen, and each $R^3$ and $R^4$ is independently hydroxyl or an acyl radical. Also of interest is an acyl derivative of a 2,2'-anyhydropyrimidine compound of formula (I), wherein $R^1$ is methyl, $R^2$ is hydrogen, and each $R^3$ and $R^4$ is an acyl radical.

In general, the ester linkage(s) of an acyl derivative of formula (I) are cleavable under physiological conditions, either in vitro, such as in a cell-based system, and/or in vivo, such as through metabolism in a body. Thus in certain embodiments, the acyl radical is a radical of a metabolite. Such acyl substituents include, but are not limited to, those derived from acetic acid, fatty acids, amino acids, lipoic acid, glycolic acid, lactic acid, enolpyruvic acid, pyruvic acid, orotic acid, acetoacetic acid, beta-hydroxybutyric acid, creatinic acid, succinic acid, fumaric acid, adipic acid, benzoic acid and p-aminobenzoic acid. Particular acyl substituents of interest are compounds which are normally present in the body, either as dietary constituents or as intermediary metabolites, and which are essentially nontoxic when cleaved from the 2,2'-anyhydropyrimidine compound of interest in vivo.

Of particular interest are compositions comprising a 3'-O-acyl-2,2'-anyhydropyrimidine or derivative thereof. For example, acyl derivatives of interest are those that include a 2,2'-anyhydropyrimidine compound of formula (I), where each $R^1$, $R^2$ and $R^3$ is independently selected from selected from hydrogen, hydroxyl, sulfyhydryl, amino, hydroxymethyl, methoxy, halogen, pseudohalogen, and a substituted or unsubstituted lower hydrocarbon containing 1 to 20 carbons, such as a lower hydrocarbon selected from alkyl, alkenyl, alkanoyl, aryl, aroyl, aralkyl and alkylamino, and esters thereof, and where $R^4$ is an O-acyl radical.

In certain embodiments, the acyl derivatives include a 2,2'-anyhydropyrimidine compound of formula (I), where $R^4$ is an O-acyl radical, and where the O-acyl radical comprises 1 to 10 carbon atoms, such as an O-acyl radical selected from aroyloxy, aralkoyloxy, heteroaroyloxy, and cycloalkoyloxy.

Accordingly, acyl derivatives of a 2,2'-anyhydropyrimidine compound of formula (I) include 3'-O-acyl-2,2'-anyhdropyrimidines, 5'-O-acyl-2,2'-anyhydropyrimidines, 3',5'-O-acyl-2,2'-anyhdropyrimidines, and derivatives thereof. For example, 3'-O-acyl-2,2'-anyhydropyrimidines or derivatives thereof include 3'-O-aroyl-2,2'-anyhydropyrimidines, such as a 3'-O-aroyl-2,2'-anyhydrouridine or derivative thereof. An example of particular interest is 3'-β-benzoyl-2,2'-anyhdrouridine or derivative thereof, such as 3'-O-benzoyl-2,2'-anhydro-5-methyluridine. Also of interest is a compound in which the 3'-β-benzoyl-2,2'-anhydro-5-methyluridine is the stereoisomer 3'-O-benzoyl-2,2'-anhydro-1-(β-D-arabinofuranosyl)-5-methyluracil.

In some embodiments, acyl derivatives of a 2,2'-anyhydropyrimidine compound of formula (I) include those where: $R^1$ is H, F, $CF_3$, $CH_3$, $CH_3CH_2$, $CH_3CH_2CH_2$, $(CH_3)_2CH$, $(CH_3)_2$ $CH_2CH_2$, $CH_3(O)CCH_2$, $CH_3(O)CCH_2CH_2$, Br—CH=CH, phenyl, benzyl, benzoyl, or benzyloxybenzyl, $R^2$ is H, OH, F, $CF_3$, $CH_3$, $CH_3CH_2$, $CH_3CH_2CH_2$, $(CH_3)_2$ CH, $(CH_3)_2CH_2CH_2$, $CH_3(O)CCH_2$, $CH_3(O)CCH_2CH_2$, Br—CH=CH, phenyl, phenyloxy, benzyl, benzyloxy, benzoyl, benzyloxybenzyl, or acyl radical, and where each $R^3$ and $R^4$ is independently hydroxyl or an acyl radical. These include the compounds: 3'-O-benzoyl-2,2'-anhydrouridine; 3'-O-benzoyl-2,2'-anhydro-5-fluorouridine; 3'-O-benzoyl-2,2'-anhydro-5-trifluoromethyluridine; 3'-O-benzoyl-2,2'-anhydro-5-methyluridine; 3'-O-benzoyl-2,2'-anhydro-5-ethyluridine; 3'-O-benzoyl-2,2'-anhydro-5-propyluridine; 3'-O-benzoyl-2,2'-anhydro-5-isopropyluridine; 3'-O-benzoyl-2,2'-O-anhydro-5-isobutyluridine; 3'-O-benzoyl-2,2'-anhydro-5-methylacyluridine; 3'-O-benzoyl-2,2'-anhydro-5-propylacyluridine; 3'-O-benzoyl-2,2'-anhydro-5-(2-bromovinyl)-uridine; 3'-O-benzoyl-2,2'-anhydro-5-phenylluridine; 3'-O-benzoyl-2,2'-anhydro-5-benzyluridine; 3'-O-benzoyl-2,2'-anhydro-5-benzyoluridine; and 3'-O-benzoyl-2,2'-anhydro-5-(benzyloxybenzyl)uridine; 5'-O-benzoyl-2,2'-anhydrouridine; 5'-O-benzoyl-2,2'-anhydro-5-fluorouridine; 5'-O-benzoyl-2,2'-anhydro-5-trifluoromethyluridine; 5'-O-benzoyl-2,2'-anhydro-5-methyluridine; 5'-O-benzoyl-2,2'-anhydro-5-ethyluridine; 5'-O-benzoyl-2,2'-anhydro-5-propyluridine; 5'-O-benzoyl-2,2'-anhydro-5-isopropyluridine; 5'-O-benzoyl-2,2'-O-anhydro-5-isobutyluridine; 5'-O-benzoyl-2,2'-anhydro-5-methylacyluridine; 5'-O-benzoyl-2,2'-anhydro-5-propylacyluridine; 5'-O-benzoyl-2,2'-anhydro-5-(2-bromovinyl)-uridine; 5'-O-benzoyl-2,2'-anhydro-5-phenylluridine; 5'-O-benzoyl-2,2'-anhydro-5-benzyluridine; 5'-O-benzoyl-2,2'-anhydro-5-benzyoluridine; and 5'-O-benzoyl-2,2'-anhydro-5-(benzyloxybenzyl)uridine; 3',5'-O-benzoyl-2,2'-anhydrouridine; 3',5'-O-benzoyl-2,2'-anhydro-5-fluorouridine; 3'5-O-benzoyl-2,2'-anhydro-5-trifluoromethyluridine; 3',5'-O-benzoyl-2,2'-anhydro-5-methyluridine; 3',5'-O-benzoyl-2,2'-anhydro-5-ethyluridine; 3',5'-O-benzoyl-2,2'-anhydro-5-propyluridine; 3',5'-O-benzoyl-2,2'-anhydro-5-isopropyluridine; 3',5'-O-benzoyl-2,2'-O-anhydro-5-isobutyluridine; 3',5'-O-benzoyl-2,2'-anhydro-5-methylacyluridine; 3',5'-O-benzoyl-2,2'-anhydro-5-propylacyluridine; 3'5-O-benzoyl-2,2'-anhydro-5-(2-bromovinyl)-uridine; 3',5'-O-benzoyl-2,2'-anhydro-5-phenylluridine; 3',5'-O-benzoyl-2,2'-anhydro-5-benzyluridine; 3'5-O-benzoyl-2,2'-anhydro-5-benzyoluridine; and 3',5'-O-benzoyl-2,2'-anhydro-5-(benzyloxybenzyl)-uridine; or the pharmaceutically acceptable salts, solvates, hydrates, and prodrug forms thereof, and stereoisomers thereof.

Of specific interest is 3'-O-benzoyl-2,2'-anhydro-5-methyluridine, 5'-O-benzoyl-2,2'-anhydro-5-methyluridine, and 3',5'-O-benzoyl-2,2'-anhydro-5-methyluridine, or the pharmaceutically acceptable salts, solvates, hydrates, and prodrug forms thereof, and stereoisomers thereof. Of specific interest are the β-D-arabinofuranosyl isomers of these compounds, or the pharmaceutically acceptable salts, solvates, hydrates, and prodrug forms thereof.

In another embodiment, compounds according to formula (I) of specific interest are those where $R^1$ and $R^4$ are as defined above, and $R^2$ and/or $R^3$ is a cyclic hydrocarbyl. By "cyclic hydrocarbyl" is intended a hydrocarbon-based ring structure having from 3 to about 10 carbon atoms, and having a single cyclic ring or multiple condensed rings that may be substituted. Cyclic hydrocarbyls of interest are selected from aryl, aralkyl, aryloxy, aroyl, aroyloxy, heteroaryl, heteroaryloxy, heteroaroyloxy, cylcoalkyl, cycloalkyloxy and cycloalkoyloxy. Thus, cyclic hydrocarbyls of special interest are O-linked to the ribose or pyrimidine ring of formula (I). Compounds where $R^2$ and/or $R^3$ is a cyclic hydrocarbyl exhibit improved activity on a molar basis, or improved specificity with respect to not interfering with MTX efficacy.

Accordingly, certain compounds of the invention comprise a 5'-O-(cyclic hydrocarbyl)-2,2'-anhydropyrimidine or derivative thereof. This embodiment includes 5'-O-(cyclic hydrocarbyl)-2,2'-anhydro-5($R^5$)-uridine or derivatives thereof, where $R^5$ is $R^1$ (e.g., $R^5$=$R^1$ where "5($R^5$)" refers to, and is the same as $R^1$ of formula (I)).

A compound of interest is 5'-O-aryl-2,2'-anhydropyrimidine or derivative thereof, of which various 2,2'-anhydrouridine derivatives are of included. This includes compounds where the 5'-O-aryl-2,2'-anhydropyrimidine is a 5'-β-aroyl-2,2'-anhydropyrimidine, such as: 5'-O-benzoyl-2,2'-anhydropyrimidine; 5'-O-chlorobenzyl-2,2'-anhydropyrimidine; 5'-O-nitrobenzyl-2,2'-anhydropyrimidine; 5'-O-hydroxybenzyl-2,2'-anhydropyrimidine, and the like.

In one embodiment, compounds that exhibit improved activity on a molar basis or improved specificity with respect to not interfering with MTX efficacy are the 5'-O-aryl-2,2'-anhydrouridines, 5'-O-aroyl-2,2'-anhydrouridines, and derivatives thereof, such as 5'-O-aryl-2,2'-anhydro-5($R^4$)-uridine, 5'-O-aroyl-2,2'-anhydro-5($R^4$)-uridine, and their derivatives. Examples include 5'-O-aryl-2,2'-anhydro-5-methyl-uridine; 5'-O-aryl-2,2'-anhydro-5-ethyl-uridine; 5'-O-aryl-2,2'-anhydro-5-propyl-uridine; 5'-O-aryl-2,2'-anhydro-5-benzyl-uridine; and 5'-O-aryl-2,2'-anhydro-5-(2-bromovinyl)-uridine; and derivatives thereof. Examples also include 5'-O-aroyl-2,2'-anhydro-5-methyl-uridine; 5'-O-aroyl-2,2'-anhydro-5-ethyl-uridine; 5'-O-aroyl-2,2'-anhydro-5-propyl-uridine; 5'-O-aroyl-2,2'-anhydro-5-benzyl-uridine; and 5-O-aroyl-2,2'-anhydro-5-(2-bromovinyl)-uridine; and derivatives thereof. Compounds of specific interest include 5'-O-benzoyl-2,2'-anhydro-5($R^4$)-uridines, such as 5'-O-benzoyl-2,2'-anhydro-5-methyl-uridine; 5'-O-benzoyl-2,2'-anhydro-5-ethyl-uridine; 5'-O-benzoyl-2,2'-anhydro-5-propyl-uridine; 5'-O-benzoyl-2,2'-anhydro-5-benzyl-uridine; and 5'-O-benzoyl-2,2'-anhydro-5-(2-bromovinyl)-uridine.

Stereoisomers of interest include the 5'-O-(cyclic hydrocarbyl)-2,2'-anhydropyrimidines which are the β-D-isomers. Examples include, but are not limited to: 5'-O-benzoyl-2,2'-anhydro-1-(β-D-arabinofuranosyl)uracil; 5'-O-benzoyl-2,2'-anhydro-1-(3-D-arabinofuranosyl)-5-fluorouracil; 5'-O-benzoyl-2,2'-anhydro-1-(β-D-arabinofuranosyl)-5-trifluoromethyluracil; 5'-O-benzoyl-2,2'-anhydro-1-(β-D-arabinofuranosyl)-5-methyluracil; 5'-O-benzoyl-2,2'-anhydro-1-(β-D-arabinofuranosyl)-5-ethyluracil; 5'-O-benzoyl-2,2'-anhydro-1-(β-D-arabinofuranosyl)-5-n-propyluracil; 5'-O-benzoyl-2,2'-anhydro-1-(β-D-arabinofuranosyl)-5-isopropyluracil; 5'-O-benzoyl-2,2'-anhydro-1-(β-D-arabinofuranosyl)-5-isobutyluracil; 5'-O-benzoyl-2,2'-anhydro-1-(β-D-arabinofuranosyl)-5-methyacyluracil; 5'-O-benzoyl-2,2'-anhydro-1-(β-D-arabinofuranosyl)-5-propylacyluracil; 5'-O-benzoyl-2,2'-anhydro-1-(β-D-arabinofuranosyl)-5-(2-bromovinyl)uracil; 5'-O-benzoyl-2,2'-anhydro-1-(β-D-arabinofuranosyl)-5-phenyluracil; 5'-O-benzoyl-2,2'-anhydro-1-(β-D-arabinofuranosyl)-5-benzyluracil; 5'-O-benzoyl-2,2'-anhydro-1-(β-D-arabinofuranosyl)-5-benzyoluracil; and 5'-O-benzoyl-2,2'-anhydro-1-(β-D-arabinofuranosyl)-5-(3-benzyoxybenzyl)uracil.

As noted above, also of interest are analogues/derivatives of the above compounds, where such analogs/derivatives reduce MTX toxicity, such that MTX toxicity is reduced when the compounds are administered in conjunction with MTX according to the subject invention. As also indicated above, an effective amount of MTX toxicity-reducing adjuvant is employed in the subject methods.

In certain embodiments, the amount of MTX toxicity-reducing adjuvant employed is more than the amount of the MTX active agent employed. In certain embodiments, the amount of MTX toxicity-reducing adjuvant is an amount that is less than equimolar to the amount of MTX active agent that is administered. Typically, the amount of toxicity-reducing adjuvant that is administered is less than about 75%, less than about 50%, less then about 25% and many embodiments less than about 15%, less than about 10% and even less than about 5% or 1% than the amount of MTX active agent. In one embodiment, the effective amount is about 1% to 50% of the amount of the MTX active agent, such as about 3% to 40%, and including about 5% to 30% of the amount of the MTX active agent. In other embodiments, the effective amount is the same as the amount of the active agent, and in certain embodiments the effective amount is an amount that is more than the amount of the MTX active agent. Effective amounts can readily be determined empirically using the data provided in the Experimental section below.

The 2,2'-anhydropyrimidine and derivatives thereof described above are commercially available or can be conventionally prepared by techniques known to one of skill in the art. For example, representative patents describing various 2,2'-anhydropyrimidine and derivatives, including intermediates and precursors, analysis, as well as the synthesis/preparation thereof, include U.S. Pat. Nos. 3,975,367; 4,145,531; 4,230,698; 4,247,544; 4,544,740; 4,604,382; 4,613,604; 4,681,933; 4,841,039; 4,916,122; 4,987,224; 5,008,384; 5,077,280; 5,084,445; 5,141,943; 5,190,926; 5,212,293; 5,278,167; 5,384,396; 5,455,339; 5,476,855; 5,596,093; 5,610,292; 5,721,241; 5,723,449; 5,739,314; 5,760,202; 5,889,013; 5,861,493; 6,060,592; 6,090,932; 6,222,025; 6,369,040; 6,642,367; 6,670,461; 6,867,290; and 7,176,295; the disclosures of which are herein incorporated by reference. See also, the following references: Veres et al., Biochem Pharmacol. 34(10):1737 (1985); Veres et al., Drugs Exp Clin Res. 13(10):615 (1987); el Konui et al, Mol. Pharmacology. 34:104 (1988); Cienfuegos et al. Org. Lett. 7(11):2161 (2005); Choi et al., Nucleosides Nucleotides Nucleic Acids 22(5-8):547 (2003); Rodriquez et al., J Med Chem 37(20): 3389 (1994); McGee, D. P. C. et al., "Novel Nucleosides via Intramolecular Functionalization of 2,2' Anahydrouridine Derivatives", Tetr. Lett., 37(12): 1995 (1996); Machulla et al. J. Nucl. Med. 42(5):257 (2001); Czernecki S. et al. Nucleosides & Nucleotides 14:1227 (1995); Heterocyclic Chemistry (3rd Edition), Thomas. L. Gilchrist, Prentice Hall (1997); Movassaghi, M. and M. D. Hill, J. Am. Chem. Soc. 128(44): 14254 (2006); Brown, D. J. Heterocyclic Compounds: The Pyrimidines. Vol 52. New York: Interscience, 1994; Eaton, (1995) Annu. Rev. Biochem. 64, 837; Usman and Cedergreen TIBS 17:334 (1992); Greene and Wuts (1991) Protective Groups in Organic Synthesis, 2nd Ed, Wiley Interscience); Moffatt, (1979) Nucleoside Analogues, Ed. Walker, N.Y., Plenum.; Townsend, (1988) Chemistry of Nucleosides and Nucleotides, NY, Plenum; and Sproat, et al., (1991) Oligonucleotides and Analogues: A Practical Approach, ed. F. Eckstein, NY. Oxford Univ. Press)).

Of particular interest are 2,2'-anhydropyrimidines and derivatives thereof that are inhibitors of uridine phosphorylase. Uridine phosphorylase (UPh; EC 2.4.2.3) is a member of the pyrimidine nucleoside phosphorylase family of enzymes which catalyzes the phosphorolytic cleavage of the C—N glycoside bond of uridine, with the formation of ribose 1-phosphate and uracil (Timofeev et al., Acta Crystallogr Sect F Struct Biol Cryst Commun., 63: 852-854 (2007)).

The scope of the present invention includes prodrugs of the MTX active agent and the MTX toxicity-reducing adjuvant. Such prodrugs are, in general, functional derivatives of the compounds that are readily convertible in vivo into the required compounds. Thus, in the methods of the present invention, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include esters that hydrolyze in vivo (e.g., in the human body) to produce a compound described herein suitable for the present invention. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates.

Formulations

Also provided are pharmaceutical compositions containing the MTX active agent and/or the MTX toxicity-reducing adjuvant employed in the subject methods. Accordingly, the MTX active agent and/or the MTX toxicity-reducing adjuvant in pharmaceutical compositions, e.g., in the form of a pharmaceutically acceptable salt, can be formulated for oral, topical or parenteral administration for use in the subject methods, as described above. In certain embodiments, e.g., where the compounds are administered as separate formulations (such as in those embodiments where they are administered sequentially), separate or distinct pharmaceutical compositions, each containing a different active agent, are provided. In yet other embodiments, a single formulation that includes both of the MTX active agent and the MTX toxicity-reducing adjuvant (i.e., one composition that includes both active agents) is provided.

By way of illustration, the MTX active agent and/or the MTX toxicity-reducing adjuvant can be admixed with conventional pharmaceutically acceptable carriers and excipients (i.e., vehicles) and used in the form of aqueous solutions, tablets, capsules, elixirs, suspensions, syrups, wafers, and the like. Such pharmaceutical compositions contain, in certain embodiments, from about 0.1% to about 90% by weight of the active compound, and more generally from about 1% to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example, a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetracetic acid, and an antioxidant, for example, sodium metabisulphite may be included in the formulation. Alternatively, the solution can be freeze dried and then reconstituted with a suitable solvent just prior to administration.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, herein incorporated by reference in its entirety. Such patches may be constructed for continuous, pulsatile, or on demand delivery of pharmaceutical agents.

In certain embodiments of interest, the MTX active agent and the MTX toxicity-reducing adjuvant are administered as a single pharmaceutical formulation, that, in addition to including an effective amount of the active agent and the toxicity-reducing adjuvant, includes other suitable compounds and carriers, and may also be used in combination with other active agents. The present invention, therefore, also includes pharmaceutical compositions comprising pharmaceutically acceptable excipients. The pharmaceutically acceptable excipients include, for example, any suitable vehicles, adjuvants, carriers or diluents, and are readily available to the public. The pharmaceutical compositions of the present invention may further contain other active agents that are well known in the art.

One skilled in the art will appreciate that a variety of suitable methods of administering a formulation of the present invention to a subject or host, e.g., patient, in need thereof, are available, and, although more than one route can be used to administer a particular formulation, a particular route can provide a more immediate and more effective reaction than another route. Pharmaceutically acceptable excipients are also well-known to those who are skilled in the art and are readily available. The choice of excipient will be determined in part by the particular compound, as well as by the particular method used to administer the composition. Accordingly, there are a wide variety of suitable formulations of the pharmaceutical composition of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The subject formulations of the present invention can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, and other such carriers that are known in the art to be appropriate.

Suppository formulations are also provided by mixing with a variety of bases such as emulsifying bases or water-soluble bases. Formulations suitable for vaginal administration may be presented as pessaries, tampons, creams, gels, pastes, foams.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Those of skill in the art will readily appreciate that dose levels can vary as a function of the specific compound, the nature of the delivery vehicle, and the like. Suitable dosages for a given compound are readily determinable by those of skill in the art by a variety of means.

The dose administered to an animal, particularly a human, in the context of the present invention should be sufficient to cause a prophylactic or therapeutic response in the animal over a reasonable time frame. One skilled in the art will recognize that dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound. Suitable doses and dosage regimens can be determined by comparisons to anticancer or immunosuppressive agents that are known to cause the desired growth inhibitory or immunosuppressive response.

Optionally, the pharmaceutical composition may contain other pharmaceutically acceptable components, such a buffers, surfactants, antioxidants, viscosity modifying agents, preservatives and the like. Each of these components is well-known in the art. For example, see U.S. Pat. No. 5,985,310, the disclosure of which is herein incorporated by reference.

Other components suitable for use in the formulations of the present invention can be found in Remington's Pharmaceutical Sciences, Mace Publishing Company, Philadelphia, Pa., 17th ed. (1985). In an embodiment, the aqueous solution of cyclodextrin also contains dextrose, e.g., about 5% dextrose.

Utility

The subject methods find use in a variety of applications. In certain applications, the methods are methods of modulating at least one cellular function, such as DHFR mediation of DNA synthesis and/or repair. In this respect, the subject methods and compositions find use in known applications of MTX, such as in treating diseases or disorders that are capable of being treated using MTX. Use of the subject compositions of the present invention is of particular utility in, for example, the treatment of diseases and disorders including, but not limited to, cancer, psoriasis, rheumatoid arthritis, Crohn's disease and tissue-graft rejection, as well as in conditions requiring immunosuppressive agents. In these capacities, use of the present inventive compositions will result in reduced toxicity while retaining the desired MTX activity.

As such, the subject methods and compositions find use in therapeutic applications in which MTX administration is indicated. A representative therapeutic application is in the treatment of cellular proliferative disease conditions, e.g., cancers and related conditions characterized by abnormal cellular proliferation. Such disease conditions include cancer and neoplastic diseases and other diseases characterized by the presence of unwanted cellular proliferation, e.g., hyperplasias, and the like. Autoimmune diseases like multiple sclerosis also feature inappropriate proliferation of immune cells.

By treatment, is meant that at least an amelioration of the symptoms associated with the condition afflicting the host is achieved, where amelioration is used in a broad sense to refer to at least a reduction in the magnitude of a parameter, e.g. a symptom associated with the condition being treated or an side effect resulting from administration of a drug. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition.

A specific application of interest is the use of anhydronucleosides, particularly 2,2'-anhydropyrimidines and derivatives thereof, to ameliorate MTX-induced mucositis. Thus, in certain embodiments, a method is provided for the treatment of a host in need thereof an effective amount of a MTX active agent in conjunction with an amount of an MTX toxicity-reducing adjuvant effective to reduce MTX-induced mucositis in the host, wherein the MTX toxicity-reducing adjuvant is a 2,2'-anhydropyrimidine or derivative thereof. In a related embodiment, the MTX-induced mucositis is stomatitis. In another related embodiment, the MTX-induced mucositis is characterized by one or more features selected from myelosuppression, weight loss, inflammation, and infection. Of specific interest is the use of 2,2'-anhydro-5-methyluridine and acyl derivatives thereof as the MTX toxicity-reducing adjuvant to reduce MTX-induced mucositis in the host.

Reduction of MTX-induced mucositis is characterized by the prevention, mitigation, or reduction of the likelihood of onset of mucositis resulting from treatment of a host with an MTX active agent. This includes treatment of a host in need thereof with an effective amount of a MTX active agent in conjunction with an amount of an MTX toxicity-reducing adjuvant effective to reduce MTX-induced mucositis in the host, where the MTX toxicity-reducing adjuvant improves the likelihood of successfully preventing or eliminating one or more features of mucositis when it has occurred including:

(i) prevention, that is, causing the clinical symptoms not to develop, e.g., preventing myelosuppression, weight loss, inflammation, and/or infection, and/or preventing progression of one or more of these features to a harmful state; (ii) inhibition, that is, arresting the development or further development of clinical symptoms, e.g., mitigating or completely inhibiting an active (ongoing) feature of mucositis so that the feature is decreased to the degree that it is no longer seriously harmful, which decrease can include complete elimination of mucositis from the host; and/or (iii) relief, that is, causing the regression of clinical symptoms, e.g., causing a relief of myelosuppression, weight loss, inflammation, infection, and/or other symptoms caused by treatment of the host with an MTX active agent.

For example, mucositis severity, including oral mucositis (stomatitis), can easily be assessed by visual inspection of mouth, throat and/or anal lesions associated with the condition, interrogation of test subjects or patients (do you have soreness of the mouth or throat?) or by use of any, or all, three well accepted disease scales: the five-grade World Health Organization (WHO) oral-toxicity scale (Miller A B et al., Cancer 1981; 47:207-214), the five-grade Radiation Therapy Oncology Group (RTOG) acute radiation-morbidity scoring criteria for mucous membranes, National Cancer Institute common toxicity criteria, version 2.0. Apr. 30, 1999 and the four-grade Western Consortium for Cancer Nursing Research (WCCNR) revised staging system for oral mucositis. Assessing stomatitis: refinement of the Western Consortium for Cancer Nursing Research (WCCNR) stomatitis staging system (Can Oncol Nurs J 1998; 8:160-165). Thus, the effect of treatment with a MTX toxicity reducing adjuvant can readily be determined using any, or all, of these test systems.

A variety of subjects are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects will be humans.

In certain embodiments, the subjects will be subjects that have been diagnosed for and are, therefore, in need of administration of the active agent. In certain embodiments, the methods may include diagnosing the subject for the presence of the disease condition to be treated by administration of the active agent.

The subject methods find use in, among other applications, the treatment of cellular proliferative disease conditions, including neoplastic disease conditions, e.g., cancers, and autoimmune diseases. In such applications, an effective amount of the MTX active agent and MTX toxicity-reducing adjuvant is administered to the subject in need thereof. Treatment is used broadly as defined above, to include at least amelioration in one or more of the symptoms of the disease, as well as a complete cessation thereof, as well as a reversal and/or complete removal of the disease condition, i.e., a cure.

There are many disorders associated with a dysregulation of cellular proliferation, e.g., cellular proliferative disorders. The conditions of interest include, but are not limited to, conditions described below.

The subject methods may be employed in the treatment of a variety of conditions where there is proliferation and/or migration of smooth muscle cells, and/or inflammatory cells into the intimal layer of a vessel, resulting in restricted blood flow through that vessel, e.g. neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Diseases where there is hyperproliferation and tissue remodeling or repair of reproductive tissue, e.g. uterine, testicular and ovarian carcinomas, endometriosis, squamous and glandular epithelial carcinomas of the cervix, etc. are reduced in cell number by administration of the subject compounds Tumors of interest for treatment include carcinomas, e.g. colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies, e.g. neuroblastoma, gliomas, etc.; hematological malignancies, e.g. childhood acute leukemia, acute myelogenous leukemias, acute lymphocytic leukemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, gestational choriocarcinoma, chorioadenoma destruens, hydatidiform mole, epidermoid cancers of the head and neck, trophoblastic neoplasms such as choriocarcinoma, chorioadenoma destruens, hydatidiform mole, etc., and the like.

Some cancers of particular interest include breast cancers, which are primarily adenocarcinoma subtypes. Ductal carcinoma in situ (DCIS) is the most common type of noninvasive breast cancer. In DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the higher the chance of lymph node metastases and the worse the prognosis is associated with greater thickness and depth of the local invasion of the melanoma. Melanoma can spread by local extension (through lymphatics) and/or by hematogenous routes to distant sites. Any organ may be involved by metastases, but lungs and liver are common sites.

Other proliferative diseases of interest relate to epidermal hyperproliferation, tissue remodelling and repair. For example, the chronic skin inflammation of psoriasis is associated with hyperplastic epidermal keratinocytes as well as infiltrating mononuclear cells, including CD4+ memory T cells, neutrophils and macrophages.

The methods of the present invention can provide a method of treating many, if not most, malignancies, including tumors derived from cells selected from skin, connective tissue, adipose, breast, lung, stomach, pancreas, ovary, cervix, uterus, kidney, bladder, colon, prostate, central nervous system (CNS), retina and blood, and the like. Representative cancers of interest include, but are not limited to, head, neck and lung tissue (e.g., head and neck squamous cell carcinoma, non-small cell lung carcinoma, small cell lung carcinoma) gastrointestinal tract and pancreas (e.g., gastric carcinoma, colorectal adenoma, colorectal carcinoma, pancreatic carcinoma); hepatic tissue (e.g., hepatocellular carcinoma), kidney and urinary tract (e.g., dysplastic urothelium, bladder carcinoma, renal carcinoma, Wilms tumor), breast (e.g., breast carcinoma); neural tissue (e.g., retinoblastoma, oligodendroglioma, neuroblastoma, and malignant meningioma; skin (e.g., normal epidermis, squamous cell carcinoma, basal cell carcinoma, melanoma, etc.).

The methods of the present invention also can provide a method of treating hematological tissues (e.g., lymphoma, chronic myeloid leukemia (CML), acute promyelocytic leukemia (APL), acute lymphoblastic leukemia (ALL), acute myeloid leukemia (AML), etc., and the like.

The dose administered to an animal, particularly a human, in the context of the present invention should be sufficient to affect a prophylactic or therapeutic response in the animal over a reasonable time frame. One skilled in the art will recognize that dosage will depend on a variety of factors including the strength of the particular compound employed, the dose of methotrexate, the dosing regimen used for methotrexate, the condition of the animal, and the body weight of the animal, as well as the severity of the illness and the stage of the disease.

The size of the dose will also be determined by the existence, nature, and extent of any adverse side-effects that might accompany the administration of a particular compound.

In the treatment of some individuals with the compounds of the present invention, it may be desirable to use a high dose regimen in conjunction with a rescue agent for non-malignant cells. In such treatment, any agent capable of rescue of non-malignant cells can also be employed, such as citrovorum factor, folate derivatives, or Leucovorin in addition to the adjuvant. Such rescue agents are well known to those of ordinary skill in the art.

Particular applications in which the subject methods and compositions find use include those described in U.S. Pat. Nos. 2,512,572; 3,892,801; 3,989,703; 4,057,548; 4,067,867; 4,079,056; 4,080,325; 4,136,101; 4,224,446; 4,306,064; 4,374,987; 4,421,913; 4,767,859; 3,981,983; 4,043,759; 4,093,607; 4,279,992; 4,376,767; 4,401,592; 4,489,065; 4,622,218; 4,625,014; 4,638,045; 4,671,958; 4,699,784; 4,785,080; 4,816,395; 4,886,780; 4,918,165; 4,925,662; 4,939,240; 4,983,586; 4,997,913; 5,024,998; 5,028,697; 5,030,719; 5,057,313; 5,059,413; 5,082,928; 5,106,950; 5,108,987; 4,106,488; 4,558,690; 4,662,359; 4,396,601; 4,497,796; 5,043,270; 5,166,149; 5,292,731; 5,354,753; 5,382,582; 5,698,556; 5,728,692; and 5,958,928; the disclosures of which are herein incorporated by reference.

Kits & Systems

Also provided are kits and systems that find use in practicing the subject methods, as described above. For example, kits and systems for practicing the subject methods may include one or more pharmaceutical formulations, which include one or both of the MTX active agent and MTX toxicity-reducing adjuvant. As such, in certain embodiments the kits may include a single pharmaceutical composition, present as one or more unit dosages, where the composition includes both the MTX active agent and MTX toxicity-reducing adjuvant. In yet other embodiments, the kits may include two or more separate pharmaceutical compositions, each containing either a MTX active agent or a MTX toxicity-reducing adjuvant.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits. For example, a kit according to one embodiment includes as a first component (a) instructions for using a MTX toxicity-reducing adjuvant, and as a second component (b) a pharmaceutical composition comprising a MTX toxicity-reducing adjuvant, a MTX active agent, or a combination thereof.

Kits of specific interest are those that include a 2,2'-anhydropyrimidine pharmaceutical composition of the invention and suitable for practicing the subject methods of the invention, such as for reducing MTX active agent-induced mucositis, including stomatitis, and such as for treatment of a cellular proliferative disorder.

The term "system" as employed herein refers to a collection of a MTX active agent and a MTX toxicity-reducing adjuvant, present in a single or disparate composition, that are brought together for the purpose of practicing the subject methods. For example, separately obtained MTX active agent and MTX toxicity-reducing adjuvant dosage forms brought together and co-administered to a subject, according to the present invention, are a system according to the present invention.

The following examples further illustrate the present invention but should not be construed in any way as limiting its scope.

EXPERIMENTAL

I. Fly Study I (Protection from Lethality)

The efficacy of cancer chemotherapy can be improved if agents are available to reduce the adverse events associated with treatment with cytotoxic agents. To this end, *Drosophila melanogaster* (commonly know as the fruit fly) is an ideal organism to screen chemical compounds for such side-effect-reducing agents. This study is aimed at finding a dose of a 2,2'-anhydropyrimidine test article that protects against MTX-induced lethality in insects.

Increasing amounts of a 2,2'-anhydropyrimidine test article (typically 0.03 to 0.1 mg) are mixed in an aqueous solution with 0.3 (or 0.4) mg MTX. Four milliliters (mL) of a 2,2'-anhydropyrimidine test article+MTX solutions are added to an appropriate amount of instant fly medium. Fruit fly eggs are added to a 2,2'-anhydropyrimidine test article+ MTX treated medium and incubated for up to 31 days. After the 31 day incubation, each assay is scored by the number of mature fly and pupae per vial.

The assays are set up in clear sterile polystyrene narrow diameter vials from Applied Scientific (Hampton, N.H.). Vials are stored in trays and incubated in a darkened 25° C. incubator.

Reagents and materials used are: 50 mg/mL MTX in $H_2O$ (pH 8), 20 mg/mL of the 2,2'-anhydropyrimidine test article in $H_2O$, water, sterile polystyrene narrow diameter vials from Applied Scientific, Instant *Drosophila* Food Medium, Oregon-R *Drosophila melanogaster,* 25° C. incubator, and 15 mL polystyrene conical tubes Each assay is performed in a separate fly vial. Increasing amounts of a 2,2'-anhydropyrimidine (0.005 to 1.0 mg) are tested for MTX side-effect-reduction on fly eggs. Amounts of the 2,2'-anhydropyrimidine test article are drawn from a 20 mg/mL stock solution dissolved in water. Nine mL of the 2,2'-anhydropyrimidine+0.3 (or 0.4) mg MTX solutions are pre-mixed with water in a 15 mL conical tube. Duplicate assays receive 4 mL of the 2,2'-anhydropyrimidine test article+0.3 (or 0.4) mg MTX solutions. Pre-measured amounts of instant *drosophila* medium are added to each assay to achieve optimal hydration level. Controls are (1) 4 mL water alone and (2) 0.3 (or 0.4) mg MTX alone. Precisely 50 fly eggs aged for ~18 hours are added to each assay. Assays are capped with a fitted plug and incubated for 30 days in a darkened 25° C. incubator. Assays are scored by the number of dead pupae or adult flies per vial.

A typical set of results of the toxicity curve for MTX in the fly model is provided in FIG. 1, which depicts the protective effect of a representative 2,2'-anhydropyrimidine test article (2,2'-anhydro-5-methyluridine, also referred to as TK-112690) on lethality in the fly model. Group 6 corresponds to the saline treated flies. Group 5 corresponds to the MTX treated flies. Groups 1-4 correspond to the MTX+TK-112690 treated flies. Doses of MTX were 0.4 mg and doses of TK-112690 ranged from 0.005 to 0.1 mg.

The data illustrated in FIG. 1 show that the effect of MTX on lethality in the flies was highly significant (p<0.01 for the difference between Groups 5 and 6), while the protection afforded by TK-112690 was highly significant (p<0.01 for the difference between Groups 1-4 and either Groups 5 or 6). These data demonstrate that 2,2'-anhydropyrimidines, such as TK-112690, reduce MTX toxicity.

II. Mouse Study I (Protection from Weight Loss)

The efficacy of cancer chemotherapy can be improved if agents are available to reduce the adverse events associated with treatment with cytotoxics. To this end, mice are an ideal organism to further analyze protecting agents originally identified in a fly model. The aim of this study is to find a dose of a representative a 2,2'-anhydropyrimidine test article that protects in a mouse against MTX-induced weight loss, a cardinal feature of mucositis.

This mouse model is modified from a published procedure (de Koning et al., Int Immunol 18: 941 (2006)). Mice are treated on day one with a single intraperitoneal (ip) dose of lipopolysaccharide (LPS), followed by two consecutive days with 200 and 100 mg/kg ip methotrexate, respectively. Controls include saline alone for days 1, 2, and 3, saline on day 1 plus MTX on days 2 and 3 and LPS on day one with saline injection on days 2 and 3. Experimental groups are given LPS on day one and 10 or 30 mg/kg, TK-112690, a representative 2,2'-anhydropyrimidine test article, ip 3 hours before, and 3 hours after, methotrexate injection on days 2 and 3. Animal weights are measured every day after the first injection with experiment termination five days after the second methotrexate injection (day 8). Weight loss is representative of MTX-induced toxicity, and one aspect of MTX-induced mucositis.

Figure 2:
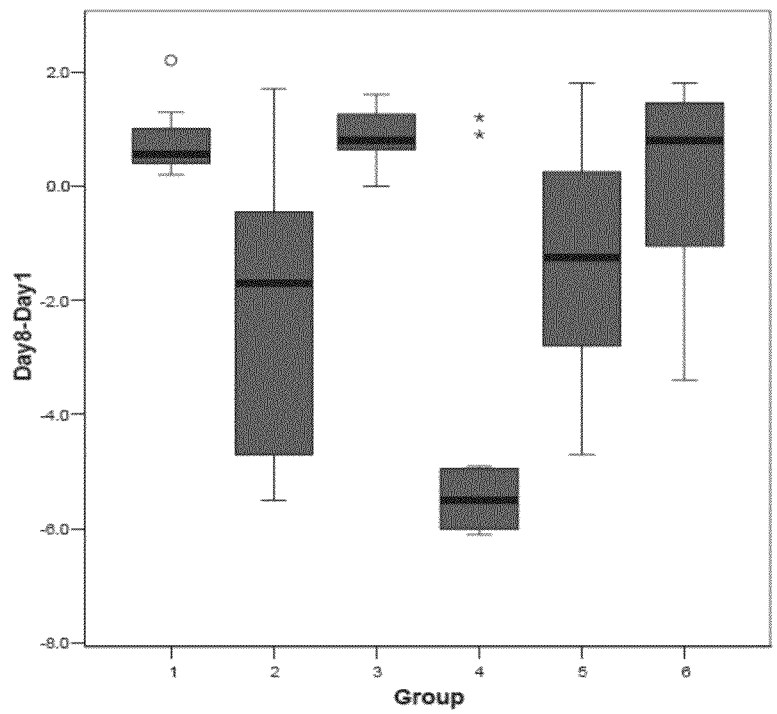
FIG. 2 depicts a set of data demonstrating the ability of TK-112690, a 2,2'-anhydropyrimidine MTX toxicity-reducing adjuvant according to an embodiment of the invention, to mitigate MTX-induced weight loss in a mammal. C57BL/6 mice (10 animals/treatment group) were dosed on Day 1 with LPS (5 µg, i.p.). On Day 2, the animals were treated with 200 mg/kg MTX+10 or 30 mg/kg TK-112690 3 hr before and 3 hr after the MTX treatment. On Day 3, the animals were dosed MTX 100 mg/kg+10 or 30 mg/kg TK±3 hr. On day 8, the Day 8-Day 1 weight was determined and results subject to ANOVA. Group 1=saline alone, Group 2=MTX alone, Group 3=LPS alone, Group 4=MTX+LPS, Group 5=10 mg/kg TK-112690+MTX+LPS or Group 6=30 mg/kg TK-112690+MTX+LPS.

Typical results for TK-112690 are presented in FIG. 2. In this plot, Group1 corresponds to the saline treated mice. Group 2 corresponds to the lipopolysaccharide (LPS) treated mice. Group 3 corresponds to the MTX treated mice. Group 4 corresponds to the LPS+MTX treated mice. Group 5 corresponds to the LPS+MTX+TK-112690 (10 mg/kg) treated mice. Group 6 corresponds to mice treated with LPS+methotrexate+TK-112690 (30 mg/kg). The ordinate in the Figure is the mean of the weight difference between studies Day 1 and 8.

The protection obtained with TK-112690 in this study was highly significant (Group 5 mean weight change versus Group 4 ($p<0.004$) and Group 6 versus Group 4 ($p<0.0005$). The effect of the 30 mg/kg dose is greater than the effect of the 10 mg/kg dose. Groups 5 and 6 are not statistically different from Group 1 (saline).

These results demonstrate that treatment with a 2,2'-anhydropyrimidine test article reduces MTX-induced toxicity in a mammalian host, and that the protective effect of 2,2'-anhydropyrimidine is dose dependent.

III. Mouse Study II (Protection from Loss of Mucosal Permeability)

The aim of this study was to evaluate the ability of a representative a 2,2'-anhydropyrimidine test article to mitigate MTX-induced loss of mucosal permeability. C57Bl/6 female mice (n=7) were treated (ip) with 100 mg/kg MTX on days 2, 3 and 4 with and without 60 mg/kg TK-112690 (ip) three hours before, and after, MTX injections. On day 7, mucosal barrier injury was estimated by measuring plasma concentrations of orally administered iodixanol determined by HPLC using UV detection. Orally administered iodixanol is not absorbed absent an increase in mucosal permeability.

Figure 3:
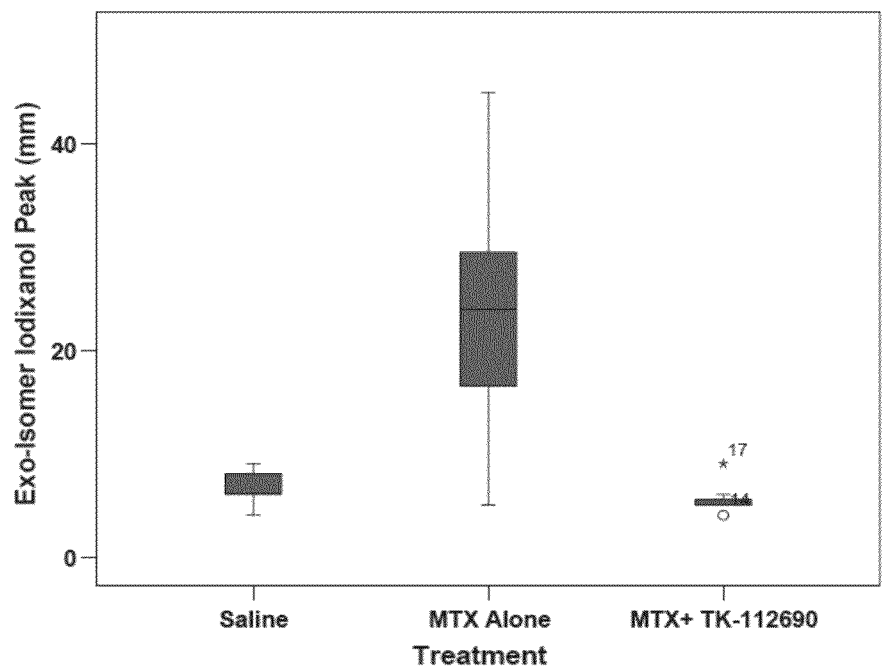
FIG. 3 depicts a set of data demonstrating the ability of TK-112690, a 2,2'-anhydropyrimidine MTX toxicity-reducing adjuvant according to an embodiment of the invention, to mitigate MTX-induced loss of mucosal permeability in a mammal. C57Bl/6 female mice (n=7) were treated intraperitoneal (ip) with 100 mg/kg MTX on days 2, 3 and 4 with and without 60 mg/kg TK-112690 (ip) three hours before, and after, MTX injections. On day 7, mucosal barrier injury was estimated by measuring plasma concentrations of orally administered iodixanol determined by HPLC using UV detection (Boxplots with minimum and maximum values (black lines). Orally administered iodixanol is not absorbed absent an increase in mucosal permeability. Group 1=saline control, Group 2=MTX and Group 3=MTX+TK-112690.

Data from the study are provided in FIG. 3. In this Figure, Group 1 is the saline control treated animals, Group 2 is the methotrexate alone treated animals and Group 3 is the methotrexate plus TK-112690 treated animals. Mice treated with 100 mg/kg MTX on Days 2, 3 and 4 experienced mucosal barrier injury indicated by increased plasma concentration of orally administered iodixanol. Co-administration of 60 mg/kg TK-112690 three hours before and three hours after MTX protected mice from MTX-induced mucosal barrier injury indicated by reduced plasma concentration of orally administered iodixanol. The results were statistically significant ($p<0.05$).

In summary, MTX administered ip to mice caused small intestinal mucosal barrier injury indicated by increased plasma concentration of orally administered iodixanol, and co-administration of TK-112690 with MTX protects against MTX-induced mucosal barrier injury indicated by reduction in plasma concentration of orally administered iodixanol.

IV. Mouse Study III (Infection Study)

The aim of this study is to examine the ability of a representative a 2,2'-anhydropyrimidine test article to mitigate MTX-induced infection measured as white blood cell counts in a mammal. Infection is representative of MTX-induced toxicity, and one aspect of MTX-induced mucositis.

Figure 4:
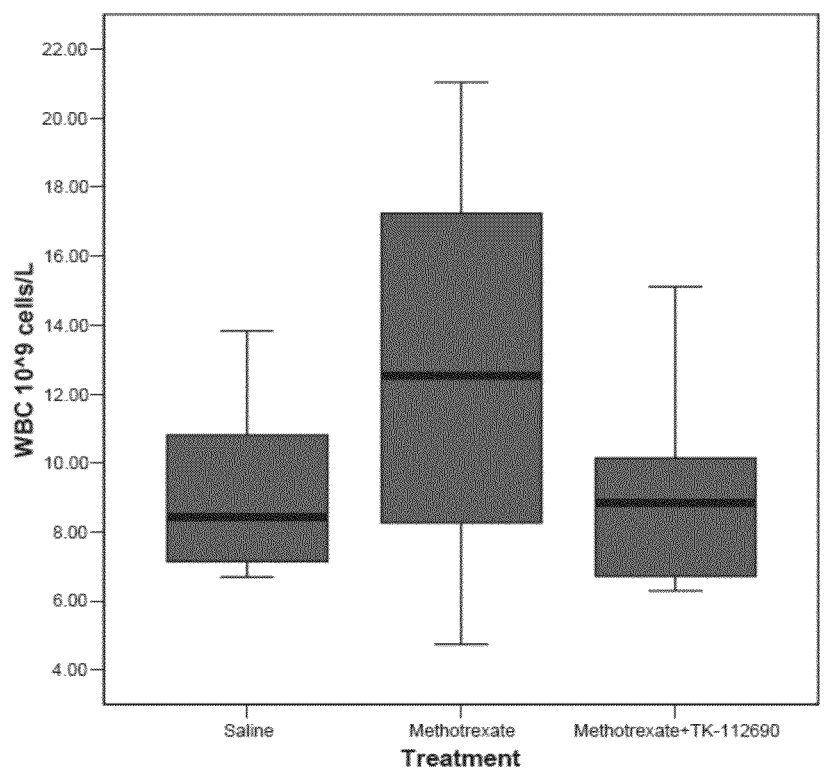
FIG. 4 depicts a set a data demonstrating the ability of TK-112690, a 2,2'-anhydropyrimidine MTX toxicity-reducing adjuvant according to an embodiment of the invention, to mitigate MTX-induced infection measured as elevated WBC concentrations in a mammal. C57BL/6 mice (n=10/dose group), treated i.p. 50 mg/kg MTX on Day 1, 2, 3, 4, 6 and 8 along with 60 mg/kg TK-112690 i.p. 3 hr±MTX followed by single daily doses TK-112690 on days not treated with MTX. On Day 11, the animals were sacrificed and hematology performed on the resulting blood. Group 1=saline control, Group 2=MTX control and Group 3=MTX+TK-112690.

Several parameters have been examined in an effort to develop a model to confirm the protection from mucositis observed in the LPS/MTX assay. On examination of complete blood counts (CBCs), consistently elevated levels of white blood cell counts (WBCs) are observed when mice are treated with MTX (FIG. 4). This increase is not observed in animals that are also treated with TK-112690 (FIG. 4). These results can be best understood by recalling that MTX damages the mucosal surface and generates a breach in the integrity of the intestinal lining, exposing the underlying tissues to bacteria. LPS is a large molecule on the outer membrane of Gram negative bacteria. Tissues exposed to LPS express pro-inflammatory cytokines such as TNF-α and IL-10. Increases in these cytokines due to exposure of tissues to LPS generate an immune response which, in turn, increases WBCs.

For the study whose data are presented in FIG. 4, C57BL/6 mice (n=10/dose group) were treated i.p. with 50 mg/kg MTX on Day 1, 2, 3, 4, 6 and 8 along with 60 mg/kg TK-112690 i.p. 3 hr±MTX followed by single daily doses TK-112690 on days not treated with MTX. On Day 11, the animals were bled and hematology performed on the resulting blood samples. Following the hematology measurements, the animals were sacrificed.

The data provided in FIG. 4 suggests that MTX treatment increases systemic WBC (the WBC level in methotrexate treated animals is statistically higher ($p<0.02$) than level in either saline or MTX+TK-112690 treated animals, which are not statistically different from one another). In summary, TK-112690 protects from MTX-induced mucositis, and that this effect can be measured by prevention of increases in WBC counts in MTX treated mice.

V. Cell Culture Study I (CCRF-CEM Human Leukemia Cells)

The aim of this study is to examine the ability of a representative a 2,2'-anhydropyrimidine test article to not interfere with the desired activity of MTX in vitro.

The following are typical data derived from screening in the human cancer cell line CCRF-CEM, which show that TK112690, a representative 2,2'-anhydropyrimidine test article, does not interfere with methotrexate cytotoxicity in this human leukemia cell line. The tumor cell line CCR-CEM (human T-cell acute lymphoblastic leukemia) is obtained from American Type Culture Collection (CRL-1593.2) and cultured in accordance with the product information sheet with the following exceptions: 55.3 $cm^2$ Petri dishes are used instead of 75 $cm^2$ culture flasks, and 1% penicillin-streptomycin solution (HyClone SV30010) and 1% GlutaMAX™ (Gibco 35050) are added to the culture medium.

TK-112690, the representative 2,2'-anhydropyrimidine test article, is dissolved in 40% DMSO, sterile filtered then diluted with sterile distilled water to obtain initial working solutions of 10, 100 and 1000 μM. In testing, a 100 fold dilution is made in culture media to give final assay concentrations of 0.1, 1.0 and 10.0 μM. MTX (SAFC Biosciences M8407) is dissolved in sterile distilled water and 5 N NaOH then sterile filtered. The final pH of the stock solution is 7.8 and working solutions are made with sterile distilled water for final assay concentrations of 30, 3.0, 0.3, 0.03 and 0.003 μM. Leucovorin (Sigma F-7878) is dissolved in sterile distilled water, sterile filtered and diluted with sterile distilled water for final assay concentrations of 0.1, 1.0 and 10.0 μM.

Aliquots of 100 μL of cell suspension are plated in 96 well microtiter plates (Corning costar 3595) and placed in an atmosphere of 5% $CO_2$ at 37° C. (Fisher Scientific Isotemp 3500 $CO_2$ Incubator). After 24 hours, 100 μL of growth medium [RPMI-1640 w/L-glutamine (Cambrex 12-702Q) fortified with sodium pyruvate (HyClone SH30239.01), fetal bovine serum (SAFC Biosciences 12107C) and HEPES buffer (Gibco 15630)] and 2 μL of test solution or vehicle are added respectively per well and the plates incubated for an additional 72 hour incubation. MTX is evaluated at concentrations of 0.003, 0.03, 0.30 and 3.0 μM alone or in combination with either a 2,2'-anhydropyrimidine test article or Leucovorin at concentrations of 0.1, 1.0, 10.0 μM. At the end of incubation, the efficacy of anti-cell proliferation is determined by optical absorbance at A=570 and 600 nm [Spectramax 250 (Molecular Devices)] in accordance with the standard alamarBlue™ (Biosource) protocol.

Figure 5:
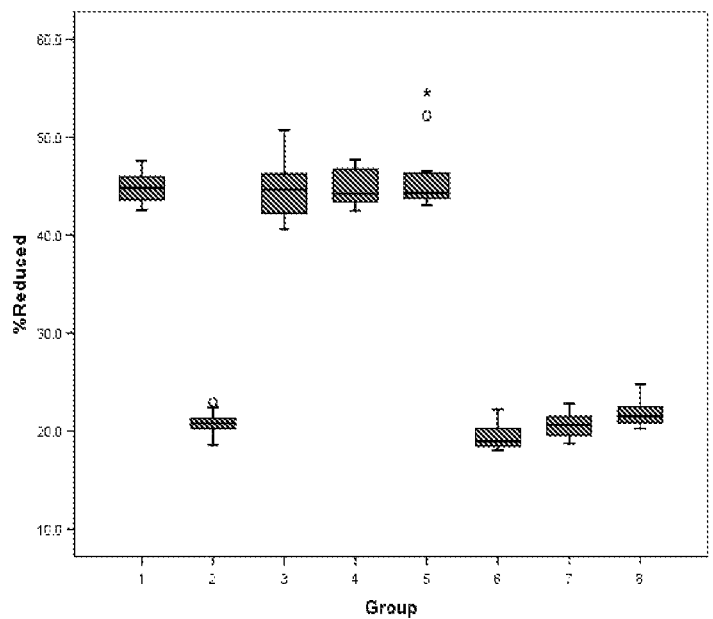
FIG. 5 depicts a set of data demonstrating that TK-112690, a 2,2'-anhydropyrimidine MTX toxicity-reducing adjuvant according to an embodiment of the invention, does not interfere with MTX cytotoxicity in human acute T-cell lymphoblastic leukemia cells (in vitro growth). In this study, CCRF-CEM cells purchased from ATCC were cultured and then 12 tubes containing approximately $10^6$ cells each treated for 72 hours with media (Group1), MTX 0.03 µM (Group2), MTX+Leucovorin 1 µM (Group3), MTX+Leucovorin 10 µM (Group4), MTX+Leucovorin 100 µM (GroupS), MTX+TK-112690 1 µM (Group6), MTX+TK-112690 10 µM (Group7) and MTX+TK-112690 100 µM (Group8). Tests with Leucovorin and TK-112690 alone were not statistically different than control (Group 1). Viability was measured as percent reduction of alamarBlue absorbance.

FIG. 5 depicts a typical set of data demonstrating that the test article does not interfere with MTX cytotoxicity. Group 1 is the cell control (media treated). Group 2 corresponds to cells treated with 0.03 µM MTX. Group 3 are cells treated with 1.0 µM Leucovorin. Group 4 are cells treated with 0.1 µM Leucovorin. Group 5 are cells treated with 10 µM TK-112690. Group 6 are cells treated with MTX+10 µM TK-112690. Group 7 are cells treated with MTX+1.0 µM TK-112690. Group 8 MTX+0.1 µM TK-112690.

Group 2 (methotrexate alone) is statistically significantly different from Group 1, 3, 4, 5, 6 and 7 ($p<0.000$, 0.000, 0.000, 0.000, 0.000, 0.000, respectively) but not different than the MTX+TK-112690 Groups (Groups 6, 7 and 8 ($p<0.844$, 0.918 and 1.000, respectively). The Leucovorin+ MTX groups (Groups 3 and 4) are statistically different than Group 2 ($p<0.000$ and 0.002, respectively) demonstrating protection by the positive control.

This human cell culture study illustrate that 2,2'-anhydropyrimidines like TK-112690 do not interfere with methotrexate cytotoxicity in a human lymphoma cell culture model.

VI. Mouse Study IV (Xenograft with CCRF-CEM Implants)

The aim of this study is to examine the ability of a representative a 2,2'-anhydropyrimidine test article to not interfere with the desired activity of MTX in vivo.

Figure 6:
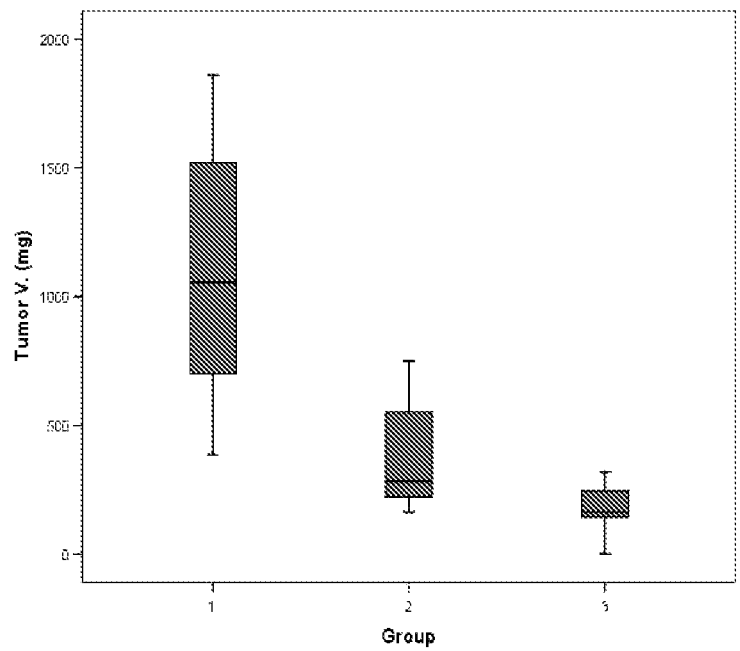
FIG. 6 depicts a set of data demonstrating that TK-112690, a 2,2'-anhydropyrimidine MTX toxicity-reducing adjuvant according to an embodiment of the invention, does not interfere with MTX cytotoxicity in human lymphoma cells (in vivo growth) implanted in a mammal. In this study, n=10 SCID mice per dose group were treated with CCRF-CEM human tumors and the tumors allowed to grow to a size of approximately 100 mg. Then the animals were treated by intraperitoneal (ip) injection with either control 20% DMSO/80% PBS (1×/day)×5 days (Group 1), MTX 7.5 mg/kg/injection (1×/day)×5 days (Group 2) or MTX 7.5 mg/kg/inj. (1×/day)×5 days+TK-112690 30 mg/kg/inj.±3 hrs (group 3). The Figure provides tumor sizes in each of the 3 groups on Day 27 of the study.

A xenograft study was performed to analyze the effect of TK-112690. administration on the in vivo efficacy of MTX against a human cancer. Human CCRF-CEM (T-ALL) cells were implanted subcutaneously into SCID mice. Tumor volumes were recorded on a regular basis, and once tumors had become established, treatment was given. Tumor volumes from day 27 of this experiment are shown in FIG. 6. Group 1 in this chart shows animals that received only saline. Group 2 shows animals treated with MTX, and Group 3 contains data from animals that received both MTX and 30 mg/kg TK-112690. All treatments were given ip, and TK-112690 was give 3 hours prior to and 3 hours after MTX administration. The results shown in FIG. 6 demonstrate that saline treated groups are significantly different from both treatment groups ($p<0.01$), however both treatment groups were not significantly different ($p=1$).

VII. Cell Culture Study II (AS283 Human Lymphoma Cells)

The aim of this study is to examine the ability of a representative a 2,2'-anhydropyrimidine test article to not interfere with the desired activity of MTX in vitro.

The following are typical data derived from screening in the human cancer cell line AS283, which show that TK112690, a representative 2,2'-anhydropyrimidine test article, does not interfere with methotrexate cytotoxicity in this human lymphoma cell line.

AS283 cells were grown in RPMI-1640 supplemented with L-glutamine dipeptide, sodium pyruvate, HEPES, and 10% FBS. AS283 cells were grown to seed three 96-well plates with 10,000 cells/well in a total volume of 50 µL. 100 µL medium in medium alone wells was seeded. Plates were incubated overnight. The following day, 25 µL of the MTX and TK-112690 stock solutions were added to the appropriate wells. TK-112690 was added first, followed by MTX in all wells. 25 µL of vehicle was added to TK-112690 alone wells. 25 µL of vehicle and 25 µL medium were added to vehicle control wells, and 50 µL medium was added to cell control wells. 10 µM doxorubicin was added as the positive control. TK-112690 concentrations were 1, 10 and 100 µM. The MTX concentrations were 0.01, 0.03, 0.1, 0.3, 1.0, 3.0, 10, 100 µM. Cell viability was measured using CellTiter-Glo and DOX (10 µM) was used as a reference standard.

The plates were incubated at 37° C., 5% $CO_2$ for 72 hours then removed from the incubator and placed on the bench at room temperature for 30 min. The plates were not stacked or shaken. 100 µL CellTiter-Glo reagent was added and mixed for 2 min, followed by a further 10 min incubation at room temperature. Luminescence was recorded on TriLux.

Figure 7:
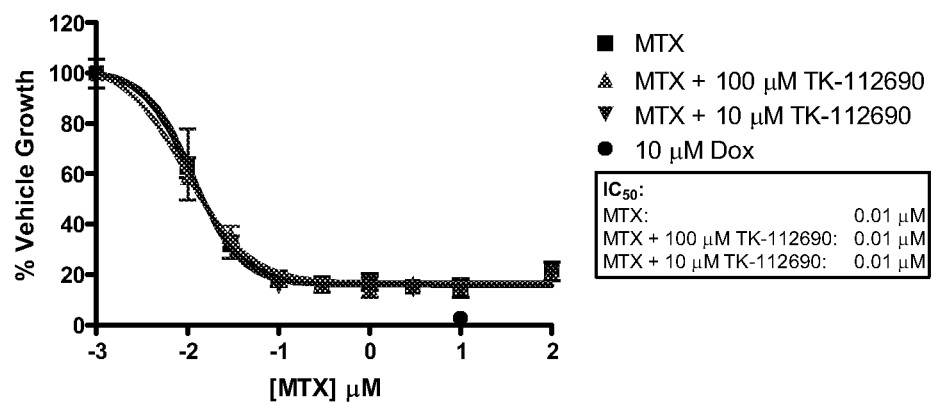
FIG. 7 depicts a set of data demonstrating that TK-112690, a 2,2'-anhydropyrimidine MTX toxicity-reducing adjuvant according to an embodiment of the invention, does not interfere with MTX cytotoxicity in human lymphoma cells (in vitro growth). In this study, AS283 cells were grown in RPMI-1640 supplemented with L-glutamine dipeptide, sodium pyruvate, HEPES, and 10% FBS. AS283 cells were used to seed three 96-well plates with 10,000 cells/well in a total volume of 50 µL. Medium alone wells were seeded 100 µL medium. Plates were incubated overnight. The following day, 25 µL of the TK-112690 and MTX stock solutions were added to the appropriate wells. TK-112690 was added first, followed by MTX in all wells. 25 µL of vehicle was added to TK-112690 alone wells. 25 µL of vehicle and 25 µL medium were added to vehicle control wells, and 50 µL medium was added to cell control wells. Cell viability was measured using CellTiter-Glo and DOX (10 µM) was used as a reference standard. The plates were incubated at 37° C., 5% $CO_2$ for 72 hours then removed from the incubator and placed on the bench at room temperature for 30 min. The plates were not stacked or shaken. 100 µL CellTiter-Glo reagent was added and mixed for 2 min, followed by a further 10 min incubation at room temperature. Luminescence was recorded on TriLux. In this study, MTX was cytotoxic to the AS283 cancer cells, but TK-112690 (1, 10, 100 µM) did not diminish the cytotoxicity of MTX (0.01, 0.03, 0.1, 0.3, 1.0, 3.0, 10, 100 µM).
Figure 7:
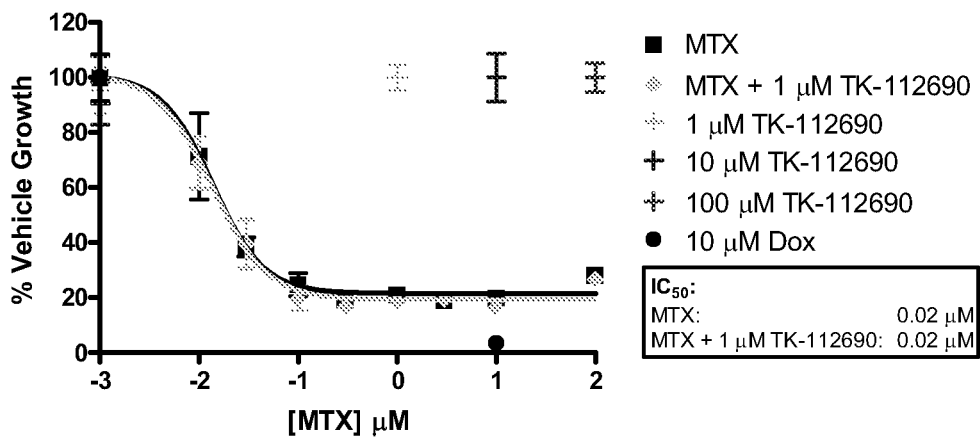

$IC_{50}$ curve for MTX and MTX+TK-112690 at 100 and 10 µM and MTX and MTX+TK-112690 1.0 µM are provided in FIG. 7. There is no statistical difference between cell viability in MTX test wells and test wells with MTX+TK-112690 (1, 10, 100 µM). Therefore, the antiproliferative activity of MTX is not altered by the addition of TK-112690. This human cell culture study illustrate that 2,2'-anhydropyrimidines like TK-112690 do not interfere with methotrexate cytotoxicity in a human lymphoma cell culture model.

VIII. Mouse Study V (Xenograft with AS283 Implants)

The aim of this study was to determine whether TK-112690 affects MTX anti-tumor efficacy against subcutaneously (sc) implanted AS283 human lymphoma xenografts in male C.B.-17 SCID mice. MTX administered alone was used as the control.

Six-week-old male C.B.-17 SCID mice were acclimated in the laboratories for seven days prior to experimentation. Thirty-to-forty mg fragments of AS283 human lymphoma tumor were implanted sc in mice near the right flank using a 12-gauge trocar needle and allowed to grow. Tumors were allowed to reach 75-198 mg in weight (75-198 $mm^3$ in size) before the start of treatment. A sufficient number of mice were implanted so that tumors in a weight range as narrow as possible were selected for the trial on the day of treatment initiation (day 8 after tumor implantation). Those animals selected with tumors in the proper size range were assigned to the various treatment groups so that the median tumor weights on the first day of treatment were as close to each other as possible (162 mg for all groups). The experiment consisted of two treatment groups and one vehicle-treated control group with ten animals per group for a total of 30 mice on the first day of treatment.

A 15 mg/mL solution of TK-112690 was prepared daily by dissolving the compound in 100% DMSO (by vortexing as needed) and then adding PBS for a 3 mg/mL dosing solution. The final composition of the vehicle was 20% DMSO/80% PBS. The 25 mg/mL stock solution of MTX for injection was diluted each day of injection with saline to a 0.75 mg/mL dosing solution. Both compounds were administered ip by exact body weight using an injection volume of 0.1 mL for every 10 g of body weight.

TK-112690 was administered by intraperitoneal (ip) injection [twice every 2 days for 5 injections with six hour interval (q6h×2, q2d×5)] at a dosage of 30 mg/kg/injection. MTX was administered by intraperitoneal (ip) injection q2d×5 at a dosage of 5.0 mg/kg/injection three hours after the TK-112690 injection. The control group was treated with both vehicles, which were administered on the corresponding compound schedules.

The sc tumors were measured and the animals were weighed thrice weekly starting the day of the first treatment. Tumor volume was determined by caliper measurements (mm) and using the formula for an ellipsoid sphere: $L \times W^2/2 = mm^3$, where L and W refer to the larger and smaller perpendicular dimensions collected at each measurement. This formula is also used to calculate tumor weight, assuming unit density (1 $mm^3$=1 mg).

The study was terminated twenty one days after tumor implantation. Any animal found moribund or any animal whose tumor reached 4,000 mg, ulcerated or was sloughed off was euthanized prior to study termination.

Figure 8:
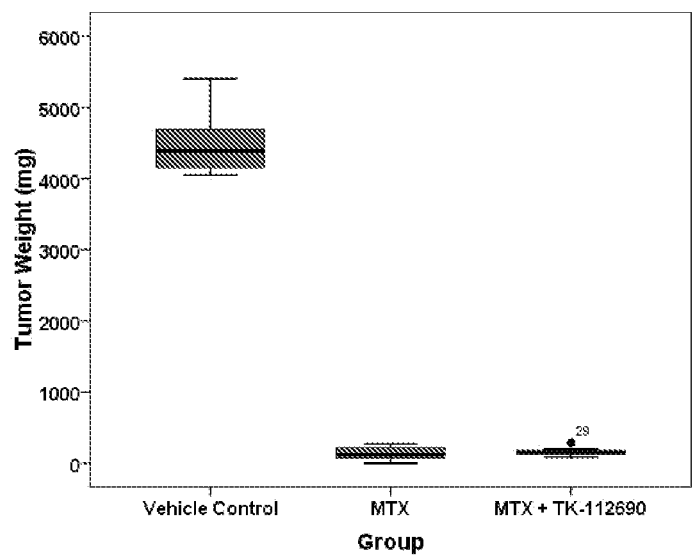
FIG. 8 depicts a set of data demonstrating that TK-112690, a 2,2'-anhydropyrimidine MTX toxicity-reducing adjuvant according to an embodiment of the invention, does not interfere with MTX cytotoxicity in human lymphoma cells (in vivo growth) implanted into a mammal. Six-week-old male SCID mice were implanted with fragments of AS283 human lymphoma tumors. The tumors were allowed to reach 75-198 mg in weight (75-198 mm$^3$ in size) before the start of treatment. The experiment consisted of two treatment groups and one vehicle-treated control group, with ten animals per group, for a total of 30 mice on the first day of treatment.

Tumor volumes on Day 21 are provided in FIG. 8. In this Figure, Group 1 is animals treated with the saline control, Group 2 is animals treated with MTX and Group 3 is animals treated with MTX+TK-112690. Tumors in the vehicle-treated control group grew to the evaluation point in all ten mice. The median tumor reached 4,387 mg in 21 days. The MTX treatment delayed the growth of AS283 lymphoma xenografts with a median tumor weight value 2.8% of the control on day 21 and a median tumor weight value of 24.7% (40.0 mg) smaller than the median tumor weight value at the start of treatment (162 mg). Administration of TK-112690 combined with MTX delayed the growth with a median tumor weight value 3.5% of the control on day 21 and a median tumor weight value 5.6% (9.0 mg) smaller than the median tumor weight value at the start of treatment (162 mg). There was no statistical difference between the MTX (Group 2) and MTX+TK-112690 (Group 3) tumor volumes (p=1.0) but both groups were statistically highly different (p<0.01) than the tumor volumes for the saline treated animals (Group1).

IX. Study with Mouse and Human Intestinal Tissue Homogenates

The aim of this study was to evaluate TK-112690 in vivo as an inhibitor of uridine phosphorylase (UPase) enzyme activity. The range of TK-112690 doses studied for ability to prevent metabolic breakdown of uridine, through the in vitro inhibition of mouse and human small intestinal UPase enzyme, was 0, 0.1, 0.5, 1, 5, 10, 50, 100, 500, 1000, 5000 and 10000 μM). Detection of UPase activity was determined by HPLC analysis using UV detection of uracil concentration (UPase catabolizes uridine into uracil and ribose-1-phosphate).

The UPase enzyme material was prepared from homogenized mouse and human being small intestinal tissue. TK-112690 was dissolved in water (50 mg/ml) and analyzed for UPase inhibition in aqueous solution containing 5 mM uridine, 0.01 M Tris, 0.01 M phosphate, 1 mM EDTA, and 1 mM DTT. Reactions were performed at 37° C. at pH of 7.3.

TK-11260 inhibition of mouse and human UPase was analyzed by reverse phase HPLC using UV detection. HPLC analysis was performed at ambient temperature with a Water 2695 Alliance system equipped with a C18 ECONOSIL 5U ALLtech column. 20 μl of UPase reaction samples were auto-injected onto column. Mobile phase consisted of water eluting for first 2.5 ml and acetonitrile gradient to 100% in 12.5 ml (flow rate 0.5 ml/min). The outlet fluent was monitored by UV absorption in the range of 240-320 nm. UPase enzymatic activity was based on the AUC of the uracil peaks.

Typical results are provided in FIG. 9. TK-112690 is seen to inhibit mouse small intestinal UPase enzyme, with a $IC_{50}$ value of 12.5 μM. TK-112690 inhibits human small intestinal UPase enzyme, with a an $IC_{50}$ value of 20.0 μM.

X. Fly Study II (UPase Knockout Fly)

The aim of this study was to evaluate the lethal effects of a range (0.001, 0.01, 0.05, 0.1, 0.2, 0.4 mg) of doses of orally fed MTX in wild-type (Ore-R) and UPase mutant *Drosophila melanogaster*. Embryos of UPase knockout (19519) *Drosophila melanogaster* were orally exposed to a dose range of MTX (0.001, 0.01, 0.05, 0.1, 0.2, 0.4 mg) in food admix. Embryos of Wild-type (Oregon-R) were orally exposed to the same dose range of MTX in presence and absence of 0.04 mg TK-112690. Scoring was based on life or death 15 days after initiation of MTX exposure.

Typical results are provided in FIG. 10. UPase knockout *D. melanogaster* (19519) is seen to be resistant to lethal effects of a dose-range (0.001, 0.01, 0.05, 0.1, 0.2, 0.4 mg) of orally administered MTX. Wild-type *D. melanogaster* is sensitive to lethal effects of 0.1 mg MTX. However, wild-type *D. melanogaster* is resistant to the lethal effects of a wide (0.001, 0.01, 0.05, 0.1, 0.2, 0.4 mg) range of orally administered doses of MTX if 0.04 mg TK-112690 is also present.

In summary, UPase knockout *D. melanogaster* are resistant to lethal effects of orally fed MTX, whereas wild-type *D. melanogater* are sensitive to MTX but are resistant to orally fed MTX in the presence of a UPase inhibitors like TK-112690

XI. Mouse Study VI (Plasma Uridine Following TK-112690 Treatment)

The aim of this study was to evaluate a range of TK-112690 doses administered to CD-1 mouse to evaluate the ability of TK-112690 to increase plasma uridine concentration through UPase inhibition.

Plasma uridine concentration was determined by HPLC using UV detectionafter animals were treated with TK-112690 as follows. TK-112690 was dissolved in PBS to achieve a concentration of 500 mg/mL. CD-1 female mice were injected ip with a range of TK-112690 doses (0, 15, 30, 60 and 120 mg/kg) and plasma from the animals analyzed for TK-112690 uridine concentrations expected to be elevated through UPase inhibition by TK-112690. Plasma uridine concentrations were determined from plasma samples collected 0.08, 0.50, 1, 2, 4 or 12 hours post TK-112690 injection.

HPLC analysis was done at room temperature using a ThermoFinnigan Spectra System equipped with degasser, pump, autosampler and UV detector. Chromatograms will be constructed from a chart recorder equipped with a pen. Analytes were separated using a Phenomenex $C_{18}$ Reverse-Phase column (250×4.6 mm). Table 2 describes gradient conditions of two separate mobile phases employed during HPLC analysis: (1) 5% methanol in nano water with 0.1% formic acid (2) 5% Methanol in Acetonitrile with 0.1% Formic acid (Flow rate=0.5 mL per minute).

TABLE 2

| Gradient Conditions HPLC Method for Plasma Uridine and TK-112690 | | |
|---|---|---|
| Time | 5% Methanol in nano water, 0.1% Formic Acid | 5% Methanol in Acetonitrile, 0.1% Formic Acid |
| 0:00 minutes | 100% | 0% |
| 10:00 minutes | 70% | 30% |
| 10:01 minutes | 0% | 100% |
| 20:00 minutes | 0% | 100% |
| 20:01 minutes | 100% | 0% |
| 40:00 minutes | 100% | 0% |

10 μL samples were auto injected onto column. Uridine, TK-112690 and 5-FU were identified by UV absorption at 262 nm. HPLC needle and injector were washed with nano water before each sample run.

The retention times of uridine, TK-112690 and 5-FU are 9.3, 8.9 and 7.7 minutes, respectively.

The micromolar concentration of plasma uridine was determined by linear equation (y=mx+b) generated from uridine and 5-FU calibration curve. The y value is calculated by taking ratio of peak heights (mm) of uridine and 5-FU. All peak heights from HPLC chromatograms were measured in millimeters using a ruler.

An identical approach was employed to quantitate TK-112690 in the samples except the response for TK-112690 was attenuated by a response factor determined from the injection into the HPLC of identical amounts of TK-112690 and uridine, Typical findings from the study are provided in FIG. 11. Plasma concentrations of TK-112690 increased with increasing doses of TK-112690 administered ip. An increase in plasma uridine is noted almost immediately following administration of TK-112690, At 0.5 hour post TK-112690 dose, a 100 μg/mL plasma concentration TK-112690 is associated with a plasma uridine concentration of approximately 2 μg/mL of uridine (baseline uridine concentration approximately 0.5 μg/mL).

XII. Synthesis of New UPase Inhibitors

A. Procedure for the Coupling of Nucleobases to Ribose Tetraacetate:

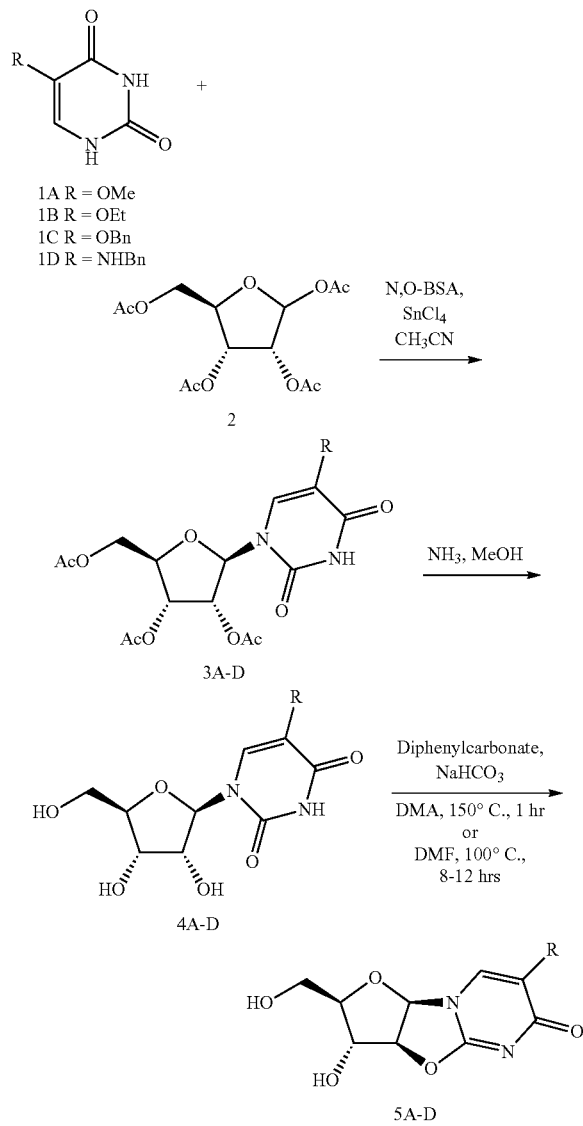

The nucleobase 1A-D (2.0 equivalents) was dissolved in dry acetonitrile (2 mL per mmol). N,O-bis-trimethylsilylamide (4.0 equivalents) was added and the mixture stirred at room temperature until clear (1-24 hours). The solution was cooled to 0° C. A solution of ribose tetraacetate (2) (1.0 equiv.) in dry CH$_3$CN (5 mL per mmol) was added slowly, followed by SnCl$_4$ (1.2 equiv.). The solution was stirred at room temperature overnight. The reaction was quenched with the careful addition of saturated aqueous sodium bicarbonate. A solution of 1M aqueous HCl was then carefully added, and the mixture stirred for one hour. The solution was extracted three times with ethyl acetate. The combined organics were washed with 1M HCl, water, saturated sodium bicarbonate and brine. The organic fraction was then dried over Na$_2$SO$_4$, filtered, and condensed in vacuo to give a crude residue that was purified by flash column chromatography (gradient, 99:1 to 90:10 chloroform:methanol) to give triacetylated ribonucleoside 3A-D.

3A: $^1$H NMR (500 MHz, CDCl$_3$) δ=9.56 (bs, 1H), 7.44 (t, J=1.5 Hz, 1H), 6.16 (d, J=4.0 Hz, 1H), 5.36-5.32 (m, 2H), 4.32 (s, 2H), 4.24 (dd, J=2.0, 13.0 Hz, 1H), 4.19 (dd, J=1.5, 13.0 Hz, 1H), 3.40 (s, 3H), 2.17 (s, 3H), 2.12 (s, 3H), 2.07 (s, 3H)

3B: $^1$H NMR (500 MHz, CDCl$_3$) δ=11.35 (bs, 1H), 7.94 (s, 1H), 5.78 (d, J=5.5 Hz, 1H), 5.37 (d, J=6.0 Hz, 1H), 5.10-5.09 (t, J=5.0 Hz, 1H), 5.07 (d, J=5.0 Hz, 1H), 4.09-4.00 (m, 3H), 3.95 (q, J=5.0 Hz, 1H), 3.83 (q, J=3.5 Hz, 1H), 3.62 (ddd, J=5.5, 8.5, 12.0 Hz, 1H), 3.53 (dt, J=4.5, 12.0 Hz, 1H), 3.41 (dq, J=1.5, 7.0 Hz, 2H), 3.32 (s, 2H), 1.09 (t, J=7.0 Hz, 3H)

3C: $^1$H NMR (500 MHz, CDCl$_3$) δ=9.01 (bs, 1H), 7.50 (m, 1H), 7.38-7.30 (m, 5H), 6.14-6.12 (m, 1H), 5.35 (d, J=4.0 Hz, 1H), 4.70 (s, 1H), 4.60 (s, 2H), 4.37-4.29 (m, 5H), 2.14 (s, 3H), 2.10 (s, 3H), 1.99 (s, 3H)

3D: $^1$H NMR (500 MHz, CDCl$_3$) δ=9.64 (bs, 1H), 7.37-7.25 (m, 5H), 6.43 (bs, 1H), 6.17 (s, 2H), 6.11 (d, J=5.5 Hz, 1H), 5.80 (dd, J=2.5, 6.5 Hz, 1H), 5.67 (dd, J=6.5, 8.0 Hz, 1H), 5.23-5.18 (m, 2H), 4.3-4.1 (m, 2H), 2.09 (s, 3H), 2.08 (s, 3H), 2.05 (s, 3H)

B. Representative Procedure for Acetate Hydrolysis Reaction:

Ribonucleoside tetraacetate 3A-D was dissolved in a 7N solution of ammonia in methanol. The solution was stirred overnight at room temperature. The solution was then reduced in vacuo. The resultant residue was triturated with ether to give the free ribonucleoside as a white solid that was isolated by filtration and dried under high vacuum before the next step.

C. Representative Procedure for Ring Closure Reactions:

Method A: The ribonucleoside (1.0 equiv.) was dissolved in anhydrous dimethylacetamide (100 μL per mmol). Diphenylcarbonate (1.0 equiv.) and sodium bicarbonate (0.05 equiv.) were added and the mixture was stirred at 150° C. for one hour. Ether was added to precipitate the product as a gum. The solvent was decanted and the crude residue was purified by either flash column chromatography or preparative HPLC.

Method B: The ribonucleoside (1.0 equiv.) was dissolved in anhydrous dimethylformamide (100 μL per mmol). Diphenylcarbonate (1.0 equiv.) and sodium bicarbonate (0.05 equiv.) were added and the mixture was stirred at 100° C. for 8-12 hours. Ether was added to precipitate the product as a gum. The solvent was decanted and the crude residue was purified by either flash column chromatography or preparative HPLC.

5A: $^1$H NMR (500 MHz, DMSO$_{d6}$) δ=7.73 (s, 1H), 6.34 (d, J=5.7 Hz, 1H), 5.86 (d, J=4.3 Hz, 1H), 5.19 (d, J=5.7 Hz, 1H), 4.95 (t, J=5.0 Hz, 1H), 4.37 (d, J=4.3 Hz, 1H), 4.10-4.04 (m, 2H), 3.30 (s, 3H)

5B: $^1$H NMR (500 MHz, DMSO$_{d6}$) δ=7.71 (s, 1H), 6.36 (d, J=5.7 Hz, 1H), 5.88 (bs, 1H), 5.19 (d, J=5.7 Hz, 1H), 4.95 (t, J=5.2 Hz, 1H), 4.41 (bs, 1H), 4.11 (dd, J=1.4, 4.0 Hz, 2H), 3.49 (q, J=7.0 Hz, 2H), 3.28-3.22 (m, 1H), 3.19-3.13 (m, 1H), 1.14 (t, J=7.0 Hz, 3H)

5C: $^1$H NMR (500 MHz, DMSO$_{d6}$) δ=7.79 (t, J=1.5 Hz, 1H), 7.38-7.34 (m, 4H), 7.32-7.27 (m, 1H), 6.36 (d, J=5.5 Hz, 1H), 5.88 (bs, 1H), 5.74 (s, 1H), 5.20 (d, J=5.5 Hz, 1H), 4.96 (t, J=5.0 Hz, 1H), 4.56 (s, 2H), 4.38 (bs, 1H), 4.20-4.19 (m, 2H), 4.09-4.05 (m, 2H), 3.28-3.27 (m, 1H), 3.19-3.15 (m, 3H)

5D: ¹H NMR (500 MHz, DMSO$_{d6}$) δ=7.31 (m, 4H), 7.22 (m, 1H), 6.64 (s, 1H), 6.20 (d, J=5.7 Hz, 1H), 5.83 (d, J=3.9 Hz, 1H), 5.46 (t, J=6.4 Hz, 1H), 5.10 (d, J=5.7 Hz, 1H), 4.93 (t, J=5.3 Hz, 1H), 4.33 (bs, 1H), 4.17-4.05 (m, 3H), 3.99 (t, J=5.3 Hz, 1H), 3.18-3.14 (m, 2H), 3.05-3.00 (m, 1H)

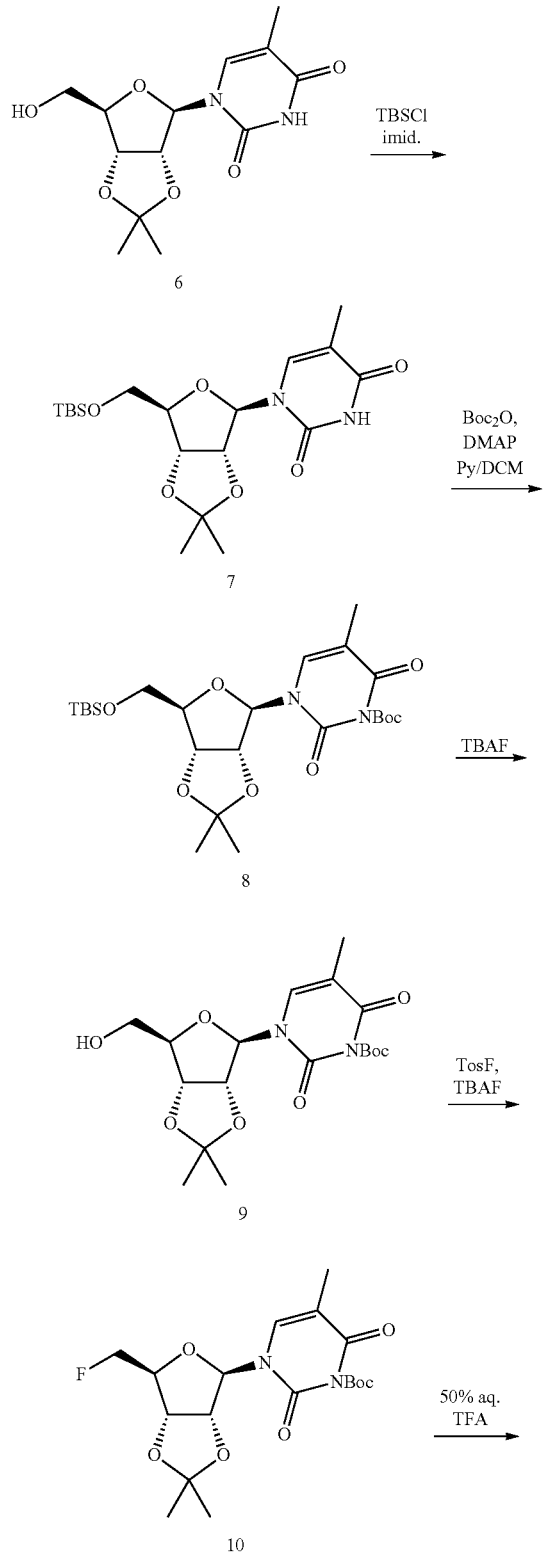

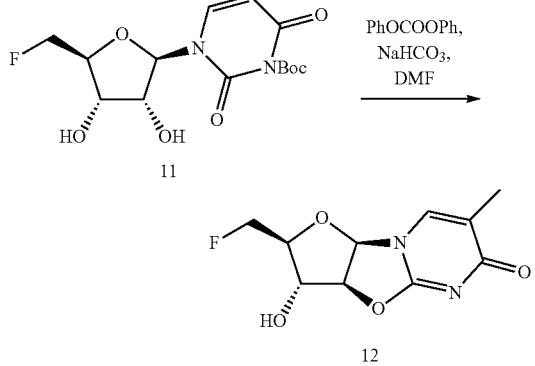

D. 2,2'-anhydro-5'-Fluoro-5-methyluridine 5-methyluridine-2',3"-acetonide 6 (5.6 g, 18.8 mmol, 1.0 equiv.) was dissolved in anhydrous dichloromethane (80 mL) and cooled to 0° C. Imidazole (2.6 g, 37.6 mmol, 2.0 equiv.) and tert-butylchlorodiphenylsilane (2.8 g, 18.8 mmol, 1.0 equiv.) were added and the mixture was allowed to warm to room temperature and stirred for one hour. The dichloromethane was removed by rotary evaporation and the residue was dissolved in 200 mL ethyl acetate, washed with water followed by brine, and dried over Na$_2$SO$_4$. Following filtration and solvent removal, the compound was purified by flash column chromatography to give 7 (6.8 g, 88%). ¹H NMR (500 MHz, CDCl$_3$) δ=9.13 (s, 1H), 7.31 (s, 1H), 5.92 (d, J=3.0 Hz, 1H), 4.76 (dd, J=3.0, 6.5 Hz, 1H), 4.72 (dd, J=2.0, 6.5 Hz, 1H), 4.27 (q, J=3.0 Hz, 1H), 3.91 (dd, J=2.5, 11.5 Hz, 1H), 3.80 (dd, J=3.5, 11.5 Hz, 1H), 1.91 (s, 3H), 1.58 (s, 3H), 1.35 (s, 3H), 0.90 (s, 9H), 0.09 (s, 3H), 0.09 (s, 3H); ¹³C NMR (125 MHz, CDCl$_3$) δ=163.98, 150.32, 136.35, 114.26, 110.80, 91.95, 86.11, 84.73, 80.36, 63.27, 27.21, 25.83, 25.30, 18.31, 12.40, -5.44, -5.54

Compound 7, (4.8 g, 1.0 equiv.) was dissolved in a 4:1 mixture of pyridine and CH$_2$Cl$_2$ (75 mL). Boc anhydride (5.2 g, 4.0 equiv.) was added, followed by DMAP (200 mg, cat.) and the solution was stirred at room temperature overnight. The solvent was removed by rotary evaporation and the residue was purified by flash column chromatography to give 8 (4.8 g, 80%). ¹H NMR (500 MHz, CDCl$_3$) δ=7.31 (s, 1H), 5.82 (d, J=3.0 Hz, 1H), 4.74 (dd, J=3.0, 6.0 Hz, 1H), 4.71 (dd, J=2.5, 6.0 Hz, 1H), 4.28 (q, J=3.0 Hz, 1H), 3.87 (dd, J=3.0, 11.5 Hz, 1H), 3.75 (dd, J=1.5, 11.5 Hz, 1H), 1.88 (s, 3H), 1.56 (s, 9H), 1.53 (s, 3H), 1.32 (s, 3H), 0.88 (s, 9H), 0.06 (s, 3H), 0.05 (s, 3H) ¹³C NMR (125 MHz, CDCl$_3$) δ=161.45, 148.41, 147.80, 136.68, 114.04, 110.14, 92.82, 86.60, 84.96, 80.46, 63.28, 27.32, 27.15, 25.78, 25.24, 18.23, 12.48, -5.51, -5.58

Compound 8, (4.8 g, 1.0 equiv.) was dissolved in anhydrous THF (333 mL). TBAF (14 mL, 1M in THF, 1.5 equiv) was added in one portion and the solution was stirred for 2 hours at room temperature. Solvent was removed by rotary evaporation and the resultant residue was purified by flash column chromatography to give 9 (2.7 g, 72%). ¹H NMR (500 MHz, CDCl$_3$) δ=7.18 (s, 1H), 5.54 (d, J=3.0 Hz, 1H), 5.08 (dd, J=3.0, 6.0 Hz, 1H), 4.97 (dd, J=4.0, 7.0 Hz, 1H), 4.27 (q, J=3.0 Hz, 1H), 3.20 (dd, J=2.5, 12.5 Hz, 1H), 3.79 (dd, J=3.0, 12.5 Hz, 1H), 1.93 (s, 3H), 1.60 (s, 9H), 1.57 (s, 3H), 1.36 (s, 3H)

Compound 9 (2.2 g, 1.0 equiv.) was dissolved in anhydrous THF under an atmosphere of nitrogen. Tosyl fluoride (1.92 g, 2.0 equiv.) was added, followed by 16.5 mL of a 1M solution of TBAF in THF (3.0 equiv.) The mixture was heated to 60° C. and stirred at this temperature for 12 hours. Upon cooling, the solvent was removed and the residue purified by flash column chromatography to give compound 10, (1.76 g, 80%). $^1$H NMR (500 MHz, CDCl$_3$) δ=7.13 (s, 1H), 5.83 (s, 1H), 4.93-4.91 (m, 1H), 4.87 (dd, J=4.0, 6.5 Hz), 4.75-4.57 (m, 2H), 4.41-4.35 (m, 1H), 1.93 (s, 3H), 1.60 (s, 9H), 1.58 (s, 3H), 1.36 (s, 3H)

Compound 10 (1.6 g, 1.0 equiv.) was dissolved in 16 mL of 50% aqueous TFA and stirred for two hours. The solvent was removed by rotary evaporation and azeotroped three times with toluene, followed by two times with CH$_2$Cl$_2$ to give 1.09 g (quant.) of the fully deprotected compound II as a white foam. $^1$H NMR (500 MHz, DMSO$_{d6}$) δ=11.36 (s, 1H), 7.39 (s, 1H), 5.78 (d, J=5.0 Hz, 1H), 4.70-4.63 (m, 1H), 4.60-4.53 (m, 1H), 4.04 (t, J=5.0 Hz, 1H), 3.99-3.93 (m, 2H), 1.78 (s, 3H)

Cyclization was performed via Method B above to give compound 12 as an off-white solid (130 mg, purified by recrystallization from ethanol/ether). $^1$H NMR (500 MHz, DMSO$_{d6}$) δ=7.70 (d, J=1.0 Hz, 1H), 6.33 (d, J=5.5 Hz, 1H), 6.11 (bs, 1H), 5.21 (d, J=5.5 Hz, 1H), 4.45-4.25 (m, 4H), 1.78 (s, 3H); $^{13}$C NMR (125 MHz, DMSO-d) δ=171.53, 159.34, 132.07, 116.68, 94.19, 90.11, 88.10, 86.32, 86.19, 83.18, 81.84, 74.51, 74.47, 13.27

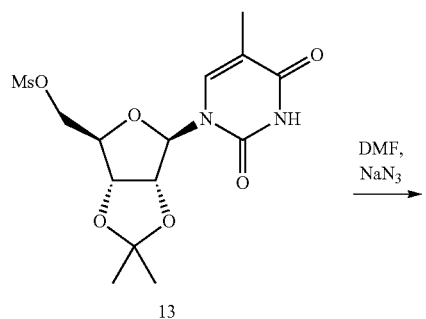

13

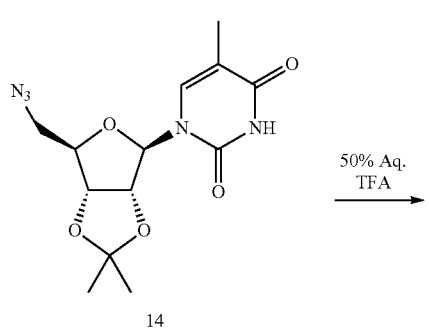

14

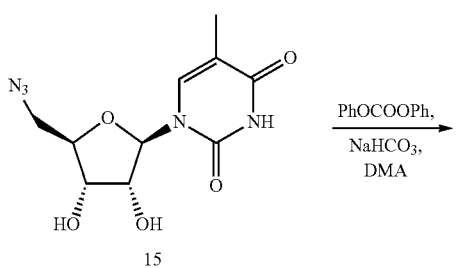

15

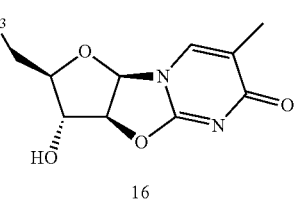

16

E. 2,2'-anhydro-5'-Azido-5-methyluridine

To a solution of Compound 13 (2.52 g, 1.0 equiv.) in 16 mL of DMF was added sodium azide (1.74 g, 4.0 equiv.). The solution was allowed to stir at room temperature overnight and solvent was removed by rotary evaporation. The crude product was purified by silica gel column chromatography to give 14 (2.16 g, quantitative yield). $^1$H NMR (500 MHz, CDCl$_3$) δ=10.11, (bs, 1H), 7.13 (d, J=1.5 Hz, 1H), 5.65 (d, J=1.5 Hz, 1H), 5.05 (dd, J=2.0, 6.5 Hz, 1H), 4.84 (dd, J=4.5, 6.5 Hz, 1H), 4.24 (dd, J=4.5 Hz, 10.5 Hz, 1H), 3.66-3.60 (m, 2H), 1.92 (d, J=1.5 Hz, 3H), 1.56 (s, 3H), 1.35 (s, 3H)

Compound 14 (0.9 g, 1.0 equiv.) was deprotected in the same fashion as compound 10. After azeotropic removal of solvent, the crude oil was triturated with diethyl ether and the resulting solid was filtered and dried to yield 15 (0.42 g, 54%). $^1$H NMR (500 MHz, DMSO$_{d6}$) δ=11.36 (bs, 1H), 7.51 (s, 1H), 5.78 (d, J=6.0 Hz, 1H), 5.40 (bs, 1H), 5.25 (bs, 1H), 4.15 (t, J=5.5 Hz, 1H), 3.94-3.88 (m, 2H), 3.59 (d, J=5.0 Hz, 2H), 1.79-1.80 (m, 3H).

Cyclization of 15 (0.4 g, 1.4 mmol, 1.0 equiv.) was performed via Method B and purified by silica gel column chromatography to give 16 (83 mg, 22%). $^1$H NMR (500 MHz, DMSO$_{d6}$) δ=7.80 (d, J=1.0 Hz, 1H), 6.33 (d, J=6.0 Hz, 1H), 6.05 (d, J=4.5 Hz, 1H), 5.22 (dd, J=1.0, 6.0 Hz, 1H), 4.32-4.29 (m, 1H), 4.2 (ddd, J=2.5, 4.0, 7.5 Hz, 1H), 3.41 (dd, J=4.0, 13.5 Hz, 1H), 3.18 (dd, J=7.5, 13.5 Hz, 1H), 1.79 (d, J=1.0 Hz, 3H).

XIII. Assay Results from Synthesized Compounds

Some compounds synthesized according to the approaches described in Experiment XII were evaluated using the test methods from Experiment I (Fly Study I, Protection from Lethality) and Experiment IX (Mouse Study with Mouse and Human Intestinal Tissue Homogenates). The results of the evaluations are provided in Table 3.

TABLE 3

Comparison of Protection from Fly Lethality and UPase Inhibition for Synthesized Compounds

| Structure | Designation | Flies Alive (Number) | UPase IC$_{50}$ (μM) |
|---|---|---|---|
| NHBn structure | TK-000006 | 0 | <100 |

TABLE 3-continued

Comparison of Protection from Fly Lethality and UPase Inhibition for Synthesized Compounds

| Structure | Designation | Flies Alive (Number) | UPase IC$_{50}$ (μM) |
|---|---|---|---|
| (EtO-substituted bicyclic nucleoside) | TK-000007 | 3 | <100 |
| (BnO-substituted bicyclic nucleoside) | TK-000008 | 0 | <100 |
| (MeO-substituted bicyclic nucleoside) | TK-000009 | 5 | <100 |
| (acetimidate ester bicyclic nucleoside) | TK-000010 | 0 | >100 |
| (5'-azido, 5-methyl bicyclic nucleoside) | TK-000011 | 0 | >100 |
| (5'-fluoro, 5-methyl bicyclic nucleoside) | TK-000015 | 0 | >100 |
| (4-methylphenylthiomethyl bicyclic nucleoside) | TK-000016 | 0 | <100 |
| (5-methyl bicyclic nucleoside) | TK-112690 | 8 | <100 |
| — | MTX Alone | 0 | — |
| — | Control | 123 | 0 |

Several compounds (TK-000006, TK-000007 TK-000008, TK-000009 and TK-100616) were active inhibitors of murine UPase (UPase IC$_{50}$<100 μM). One compound, TK000009, was also active in the Fly model for protection against MTX-induced lethality. To date all compounds active in the Fly model are also active UPase inhibitors. However, not all active UPase inhibitors are also active protectants in the Fly model.

It is evident from the above results that the subject invention provides for methods of reducing the toxicity of MTX active agents while retaining their desired activity. As such, the subject invention finds use in a variety of different applications and represents a significant contribution to the art.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of administering to a host in need thereof an effective amount of a methotrexate (MTX) active agent, said method comprising: administering to said host a composition comprising said effective amount of an MTX active agent as the only active agent in the composition in conjunction with an amount of an MTX toxicity-reducing adjuvant effective to reduce toxicity of said MTX active agent, wherein said MTX toxicity-reducing adjuvant is a 2,2'-anhydropyrimidine.

2. The method according to claim 1, wherein said 2,2'-anhydropyrimidine is a compound of formula (I):

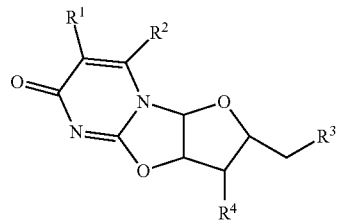

wherein:
each $R^1$, $R^2$, $R^3$ and $R^4$ is independently selected from the group consisting of hydrogen, substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, carbohydrate, nucleic acid, amino acid, peptide, dye, fluorophore and polypeptide;
or a pharmaceutically acceptable salt thereof.

3. The method according to claim 2, wherein each $R^1$, $R^2$, $R^3$ and $R^4$ is independently selected from the group consisting of hydrogen, hydroxyl, sulfhydryl, amino, hydroxymethyl, methoxy, halogen, pseudohalogen, and a substituted or unsubstituted lower hydrocarbon containing 1 to 20 carbons.

4. The method according to claim 3, wherein said lower hydrocarbon is selected from the group consisting of alkyl, alkenyl, alkanoyl, aryl, aroyl, aralkyl and alkylamino, and esters thereof.

5. The method according to claim 2, wherein $R^1$ is hydrogen, fluorine, methyl, ethyl, propyl, benzyl, 2-bromovinyl, $CH_3CH_2OCH_2—$ or $CH_3OCH_2—$; $R^2$ is hydrogen, hydroxyl, fluorine, methyl, ethyl, propyl, benzyl, benzoyl, benzoyloxy, or 2-bromovinyl; and each $R^3$ and $R^4$ is independently selected from the group consisting of hydroxyl and benzoyloxy.

6. The method according to claim 5, wherein $R^1$ is hydrogen or methyl; $R^2$ is hydrogen; and each $R^3$ and $R^4$ is independently selected from the group consisting of hydroxyl and benzoyloxy.

7. The method according to claim 5, wherein $R^1$ is methyl; $R^2$ is hydrogen; and each of $R^3$ and $R^4$ are hydroxyl.

8. The method according to claim 1, wherein said toxicity of said MTX active agent is mucositis.

9. A pharmaceutical composition comprising an effective amount of an MTX active agent as the only active agent in the composition and an effective amount of an MTX toxicity-reducing adjuvant in a pharmaceutically acceptable vehicle, wherein said MTX toxicity-reducing adjuvant is a 2,2'-anhydropyrimidine.

10. The pharmaceutical composition according to claim 9, wherein said 2,2'-anhydropyrimidine is a compound of formula (I):

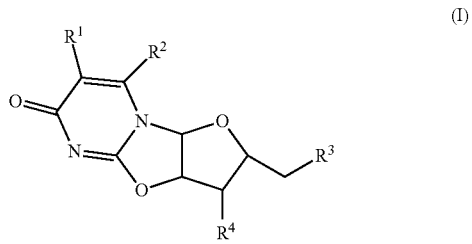

wherein:
each $R^1$, $R^2$, $R^3$, and $R^4$ is independently selected from the group consisting of hydrogen, substituted or unsubstituted heteroatom, substituted or unsubstituted alkyl, substituted or unsubstituted cycloalkyl, substituted or unsubstituted heterocycloalkyl, substituted or unsubstituted aryl, substituted or unsubstituted heteroaryl, substituted or unsubstituted aralkyl, carbohydrate, nucleic acid, amino acid, peptide, dye, fluorophore and polypeptide;
or a pharmaceutically acceptable salt thereof.

11. The pharmaceutical composition according to claim 10, wherein each $R^1$, $R^2$, $R^3$, and $R^4$ is independently from selected from the group consisting of hydrogen, hydroxyl, sulfhydryl, amino, hydroxymethyl, methoxy, halogen, pseudohalogen, and a substituted or unsubstituted lower hydrocarbon containing 1 to 20 carbons.

12. The pharmaceutical composition according to claim 11, wherein said lower hydrocarbon is selected from the group consisting of alkyl, alkenyl, alkanoyl, aryl, aroyl, aralkyl and alkylamino, and esters thereof.

13. The pharmaceutical composition according to claim 11, wherein $R^1$ is hydrogen, fluorine, methyl, ethyl, propyl, benzyl, 2-bromovinyl, $CH_3CH_2OCH_2—$ or $CH_3OCH_2—$; $R^2$ is hydrogen, hydroxyl, fluorine, methyl, ethyl, propyl, benzyl, benzoyl, benzoyloxy, or 2-bromovinyl; and each $R^3$ and $R^4$ is independently selected from the group consisting of hydroxyl and benzoyloxy.

14. The pharmaceutical composition according to claim 13, wherein $R^1$ is hydrogen or methyl; $R^2$ is hydrogen; and each $R^3$ and $R^4$ is independently selected from the group consisting of hydroxyl and benzoyloxy.

15. The pharmaceutical composition according to claim 13, wherein $R^1$ is methyl; $R^2$ is hydrogen; and each of $R^3$ and $R^4$ are hydroxyl.

16. A method of administering to a host in need thereof an effective amount of a methotrexate (MTX) active agent, said method comprising administering to said host a pharmaceutical composition consisting of:
said effective amount of a MTX active agent;
an effective amount of a MTX toxicity-reducing adjuvant that is a 2,2'-anhydropyrimidine; and
a pharmaceutically acceptable vehicle.

17. A pharmaceutical composition consisting of:
an effective amount of a MTX active agent;
an effective amount of a MTX toxicity-reducing adjuvant that is a 2,2'-anhydropyrimidine; and
a pharmaceutically acceptable vehicle.

* * * * *